United States Patent [19]
Khutoryansky et al.

[11] Patent Number: 5,917,882
[45] Date of Patent: Jun. 29, 1999

[54] RADIOGRAPHIC/FLUOROSCOPIC IMAGING SYSTEM WITH REDUCED PATIENT DOSE AND FASTER TRANSITIONS BETWEEN RADIOGRAPHIC AND FLUOROSCOPIC MODES

[75] Inventors: Oscar Khutoryansky, Glenview; Thomas Rosevear, Forest Park; Cyril Tomsic, Hanover Park; Yevgeniy Maltsev, Skokie; Thomas Simak, Warrenville; James Taylor, Glen Ellyn, all of Ill.

[73] Assignee: Continental X-Ray Corporation, Broadview, Ill.

[21] Appl. No.: 08/753,772

[22] Filed: Nov. 29, 1996

[51] Int. Cl.$^6$ .................................................. H05G 1/64
[52] U.S. Cl. ..................... 378/116; 378/98.7; 378/108; 378/98.2
[58] Field of Search ................................. 378/116, 108, 378/98.7, 97

[56] References Cited

U.S. PATENT DOCUMENTS

| | | | |
|---|---|---|---|
| 4,185,198 | 1/1980 | Fujimoto | 378/116 |
| 4,649,558 | 3/1987 | Brunn | 378/97 |
| 4,658,413 | 4/1987 | Nishioka et al. | 378/116 |
| 4,924,487 | 5/1990 | Nishiki | 378/116 |

*Primary Examiner*—Craig E. Church
*Attorney, Agent, or Firm*—Laff, Whitesel & Saret, Ltd.

[57] ABSTRACT

A radiographic/fluoroscopic imaging system provides rapid transition from fluoroscopic to radiographic imaging mode by maintaining the X-ray tube high voltage, increasing the filament current, allowing X-ray tube current to increase toward the desired radiographic current, and terminating exposure when the desired X-ray dose has been achieved. Rapid transition from radiographic to fluoroscopic imaging mode is provided by reducing x-ray tube high voltage to produce an equivalent fluoroscopic-level x-ray output at high initial current, dropping filament current, and enabling ABS control of the high-voltage. As x-ray tube current drops, ABS correspondingly increase high voltage to maintain the desired output. The imaging system obtains movement-related information by analyzing a video signal (such as from fluoroscopic image or an image from an optical camera trained on the patient), or from operator movement requests. The imaging system uses movement-related information to responsively control fluoroscopic pulse rate or other imaging parameters. The imaging system can also use such information to initiate a radiographic exposure, or advance to the next step of an operator programmed examination consisting of interspersed fluoroscopic and radiographic exposures. This results in a lower dose to both the patient and the examiner, consistent with high image quality.

19 Claims, 14 Drawing Sheets

RADIOGRAPHIC/FLUOROSCOPIC IMAGING SYSTEM WITH REDUCED PATIENT DOSE AND FASTER TRANSITIONS BETWEEN RADIOGRAPHIC AND FLUOROSCOPIC MODES

BACKGROUND OF THE INVENTION

This invention relates to medical diagnostic imaging systems, and more particularly, to apparatus and methods for providing highly-versatile diagnostic medical imaging systems capable of performing radiographic and fluoroscopic examinations. Still more particularly, the invention relates to radiographic/fluoroscopic imaging systems, and associated methods, which achieve rapid transitions between fluoroscopic and radiographic modes, and which employ information regarding detected, forecast, or requested motion of the patient or the imaging system in order to reduce the x-ray dose delivered to the patient and examiner.

Medical imaging systems capable of performing both fluoroscopic and radiographic examinations have become highly valuable diagnostic tools in modern radiology. An advantageous application of the dual capabilities of such imaging systems is peripheral angiography. Peripheral angiography is a diagnostic roentgenographic procedure providing visualization and recording of the blood vessels in the peripheral region of the body, such as the arms and legs. In a typical peripheral angiography examination, a radiopaque contrast agent is injected into a blood vessel, and a rapid sequence of radiographs are taken to observe the progress of the contrast agent as it flows through the vessels along the length of the extremity. The contrast agent is initially concentrated in the blood vessels and takes some time to diffuse generally into the surrounding regions. Thus, the contrast agent renders the blood vessels visible under radiography provided that the radiographs are taken very soon after the contrast agent arrives in a particular region.

In conventional Peripheral Angiography examinations, the patient is supported on a movable table top positioned under system control, The table top, in turn, is supported by a stationary radiographic-fluoroscopic table. An overhead X-ray source (which may be mounted on a tube crane) directs a beam through the patient to a "rapid film changer" device.

The locations of interest at any particular time during the examination are in the general vicinity of the leading edge of the contrast material as it progresses through the extremity. In conventional peripheral angiography systems, the rapid film changer is normally in a fixed position. Because the length of the recording radiographic film or imaging device is not sufficient to cover the entire extremity, conventional peripheral angiography systems require that the patient be rapidly repositioned throughout the procedure to fully visualize and record the contrast material as it progresses through the vessels of the extremity (i.e., the patient must be rapidly repositioned throughout the procedure to maintain the contrast material within in the field of view of the rapid film changer). In such conventional systems, the patient rests on a movable table-top, which may travel as rapidly as 9 in/sec between exposures.

Peripheral angiography is representative of mixed fluoroscopic/radiographic examinations in which the examiner, while conducting a fluoroscopic examination, desires to immediately perform a radiographic exposure of a feature or event observed on the fluoroscope. For example, when a radio-opaque dye reaches a certain position in the patient, or some other event of interest occurs during the fluoroscopic examination, it is desirable to immediately record a high-quality radiographic exposure for later use.

In conventional equipment of the type heretofore described, a mechanical operation is required in order to change from the fluoroscopic mode of operation to the radiographic mode, and vice versa. The positions of the radiographic imaging receiver (typically film) or the fluoroscopic imaging receiver (typically an image intensifier) must be exchanged, or an overlapping one of these components must be moved to expose the other. This mechanical operation, even when driven under automatic control of the imaging system, may take one to several seconds. Other time-consuming activities, such as changing certain X-ray tube operating parameters, are also required to perform the transition. However, these activities generally take less time than the mechanical operation and because they are started in parallel, they complete earlier. Accordingly, in older radiographic/fluoroscopic imaging systems, this mechanical operation has been the rate-limiting step controlling the speed at which transitions between radiographic and fluoroscopic imaging modes can be achieved.

Recently, however, filmless radiographic/fluoroscopic imaging systems have been developed which use a single image intensifier (or "photospot") device to receive and record image information during both fluoroscopic and radiographic exposures. As a result, it is not necessary to change film between exposures, nor is it necessary to perform other mechanical operations in order to change between fluoroscopic to radiographic imaging modes because there is no need move one component out of the way of another. With the elimination of mechanical operations, changing the operating current of the X-ray tube has become the rate-limiting step controlling the speed of transitions between radiographic and fluoroscopic imaging modes in filmless radiographic/fluoroscopic imaging systems.

For a particular X-ray tube employed in an imaging system, the X-ray output delivered by the X-ray tube is directly proportional to the X-ray tube current (which is typically measured in milliamperes (mA)), and is approximately proportional to the fifth power of the X-ray tube voltage (which is typically measured in kilovolts (kV). X-ray tube voltage is selected for the best image contrast, depending on the type of tissue being examined and the character of the examination.

In general, fluoroscopic exposures employ relatively low average X-Ray tube current (e.g., 0.5–3 mA (average)) over a long exposure time, while radiographic exposures use high X-Ray tube current (e.g. 100–1000 mA) over a very short time. The X-ray tube cathode operates by thermionic emission. The X-Ray tube current (i.e., the current flowing between the anode and the cathode) is a function of X-Ray tube anode-cathode voltage (or "high voltage"), X-Ray tube cathode (filament) temperature (which itself is a function of X-Ray tube filament current), and perhaps other factors. However, X-Ray tube current (for a particular selected high voltage) is generally controlled by adjusting the filament temperature, which, in turn, is controlled by adjusting the filament current.

X-Ray tubes which are suitable for both fluoroscopic and radiographic exposures may include one or two filaments of differing sizes. Where a single filament is used, and it is desired to change from fluoroscopic to radiographic mode, the filament current must be increased to allow the filament temperature to increase, thereby permitting a higher X-Ray tube current which is sufficient for radiographic exposures.

Where two filaments are provided, one filament is typically kept at a standby temperature just under the cathodic emission temperature, to avoid deterioration of the filament, except when the filament is selected for use. Thus, even for two-filament tubes, when a radiographic exposure is desired, the radiographic filament current must be increased to allow the filament to heat to a sufficient temperature.

Because it takes time to heat or cool the filament to a desired temperature, the X-ray tube current cannot be instantaneously controlled. It typically takes around one second for the filament to heat from an initial temperature (such as its temperature when operating in fluoroscopic mode or when in standby) to the temperature required for a radiographic exposure. In conventional radiographic/fluoroscopic systems, the high-voltage power supply to the tube is disabled, thereby inhibiting X-Ray emission, during the filament heating period. Thus, the radiographic exposure does not begin until after the filament reaches the required temperature. This delay can be significant, because the dye may progress a substantial distance, or a transient event may have ended, before the radiographic exposure can be recorded.

The opposite transition, from radiographic mode to fluoroscopic mode, is equally important. In radiographic mode, the system operates with relatively high x-ray tube current. Tube current is a function of the temperature of the cathode or filament, and therefore, in radiographic mode, the filament must be relatively hot to support the high required tube current. In fluoroscopic mode, much lower current, and therefore, accordingly-reduced filament temperature, is typically used. The cooling of the filament is an exponential process over time, so that the tube current cannot be instantaneously reduced to the desired level normally used for fluoroscopy. In conventional radiographic/fluoroscopic imaging systems, in which a transition from radiographic to fluoroscopic mode is desired, the system must wait for the filament to cool down to a temperature appropriate to produce the tube current desired in fluoroscopic mode. This delay is undesirable.

Another problem with prior art radiographic/fluoroscopic imaging systems is that they do not optimally minimize the radiation dose delivered to the patient (and radiologist, technician, or other examining personnel) during an examination. For example, in fluoroscopic examination systems, fluoroscopic exposures may be made continuously, at low X-ray tube current (mA), or in short, repetitive bursts or pulses, at higher tube current. In pulsed fluoroscopy, digital video memory is used to preserve the displayed image between pulses. For a selected average x-ray dose as continuous fluoroscopy, the momentary X-ray tube current is higher, resulting in higher signal-to-noise ratio.

Pulsed fluoroscopy systems may have low and high pulse repetition rates. Lower pulse repetition rates are desirable in that they result in a lower accumulated radiation dose to the patient, and any other personnel in the vicinity. When an observed scene is stationary, low-rate pulsed fluoroscopy is preferred because it results in a lower dose to the patient and the operator. However, if movement or changes occur in the observed scene, the changes appear only when the exposure pulses occur. At low repetition rates, brief transient events may be missed entirely, and movement appears jerky. It has been noted that even in radiographic/fluoroscopic imaging systems which allow the examiner to vary the pulse rate in response to patient motion, examiners often use a high pulse rate (appropriate for observing movement) throughout the examination, including those periods in which no movements or changes in the image are actually occurring or expected. This undesirably increases the radiation dose delivered to both the patient and the examiner.

Nields U.S. Pat. No. 5,119,409 discloses a pulsed fluoroscopy system which analyzes the fluoroscopic image and responsively dynamically controls the fluoroscopic pulse rate based on motion detected in the image. This system has the disadvantage that the fluoroscopic image cannot be acquired without exposing the patient to X-rays.

Another disadvantage of prior art radiographic/fluoroscopic systems is that they employ error-prone methods of determining when to initiate a radiographic exposure. The peripheral angiography examination described above is an example of a type of imaging examination to which modern imaging systems are applied in which the patient undergoes a continuous or repetitive-pulse fluoroscopic examination while the examiner awaits an event of particular interest. The event may be, for example, movement of the patient (as might occur as the patient swallows or breathes), or the arrival of a contrast medium or dye in the image or at a particular location in the image. The occurrence of the event may then trigger the desire to perform a radiographic examination, which may range from a single radiographic (or "photospot") exposure to a preprogrammed sequence of radiographic exposures and movement of the patient interspersed such that the exposures occur at various patient locations.

In prior-art radiographic/fluoroscopic imaging systems, a radiologist or technician must observe the fluoroscopic display to detect the event of interest, and then initiate the radiographic exposure (and in most cases, each individual radiographic exposure thereof). This means that the observer must have extensive training and experience and must employ careful, vigilant observation. If the radiographic examination is initiated too early or too late, or the event is missed, the results of the examination may be of poor quality or may be entirely useless; re-examination is undesirable because the patient receives additional exposure to radiation.

OBJECTS AND SUMMARY OF THE INVENTION

It is therefore an object of the present invention to provide a radiographic/fluoroscopic imaging system which avoids the problems and disadvantages of prior art imaging systems.

It is another object of the present invention to provide a radiographic/fluoroscopic imaging system which achieves rapid transitions between radiographic and fluoroscopic imaging modes.

It is a further object of the present invention to provide a radiographic/fluoroscopic imaging system which provides high image quality consistent with reduced radiation dose to the patient and examiner.

It is another object of the present invention to provide a radiographic/fluoroscopic imaging system which employs movement-related information to control the operation of the imaging system.

It is a further object of the present invention to provide a radiographic/fluoroscopic imaging system which employs movement-related information to optimally adjust the fluoroscopic pulse rate and other imaging parameters.

It is another object of the present invention to provide a radiographic/fluoroscopic imaging system which employs movement-related information to initiate a radiographic exposure upon the occurrence of an event of interest.

According to an aspect of the present invention, a radiographic/fluoroscopic imaging system provides rapid transitions from radiographic to fluoroscopic imaging modes, and vice versa. In contrast to prior art systems, when a rapid transition from fluoroscopic to radiographic mode is desired (e.g., an immediate radiographic exposure in the midst of a fluoroscopic examination), the inventive system does not disable the x-ray tube high voltage during the filament heating period. Instead, the imaging system performs following steps:

(1) the X-ray tube high voltage (kV) is held constant;

(2) the X-ray filament current is increased to that required for radiography (initiating filament heating to the temperature required to support X-ray tube current desired for radiographic exposure;

(3) the radiographic exposure begins immediately, even while the X-ray tube current increases in response to increased filament temperature; and (4) the radiographic exposure is terminated when the desired X-ray dose (effectively, X-ray tube current integrated over time mA•S has been delivered, using mA•S control or automatic exposure control (AEC).

Thus, although initially the X-ray tube current would be low, it would increase during the exposure, and a substantial fraction of the exposure would occur during the filament heating period. As a result, the inventive imaging system would allow the resulting radiograph to capture image information during the filament heating period, which information would be missed in prior art systems.

A prior art technique for minimizing total exposure time, but which does not achieve the advantages of the invention, is referred to as the "fallen load" technique. The time-vs.-power characteristics of X-ray tubes are non-linear. In order to avoid damaging the X-ray tube (e.g. by over-heating the anode), the tube may be operated at maximum power for a tiny fraction of time, but may be operated substantially longer or even continuously at reduced power. In the "fallen load" technique, total exposure time is minimized by initially operating the tube at maximum power for the rated interval. Then the operating power is reduced gradually or in stages, consistent with the tube maximum operating power specifications, until an automatic exposure control system indicates a desired total integrated exposure has been achieved. This technique optimally minimizes total exposure time, in contrast to the invention, which optimally provides at least some radiographic exposure as early as possible.

The inventive imaging system achieves a rapid transition in the opposite direction, from radiographic to fluoroscopic mode, by exploiting several known or empirically-determined relationships between x-ray tube current, x-ray tube high voltage, x-ray tube flux output, and image intensifier brightness. The X-ray tube flux output is linearly proportional to x-ray tube current (mA) but is approximately proportional to the fifth power of the high voltage ($kV^5$). For example, to double the flux output, one may double the x-ray tube current, or increase the high voltage (kV) by approximately 15 percent. Thus, within the operating limits and characteristics of a particular x-ray tube, the same output or radiation dose (which effectively corresponds to image brightness) can be achieved at various selected values of one of the tube operating parameters (tube current or high voltage), provided that the opposite parameter (high voltage or tube current, respectively) is correspondingly adjusted.

When a radiographic exposure is completed, and it is desired that the imaging system return to fluoroscopic mode, the following steps are performed:

(1) The small x-ray tube focal spot is selected (if one is available).

(2) Cooling of the x-ray tube filament, which controls current through the tube, is initiated by immediately reducing the filament current (c.f. x-ray tube current).

(3) Because the x-ray tube cathode (filament) cannot be instantaneously cooled, the x-ray tube current is initially that which was used during the immediately previous radiographic exposure. The tube current will decay over time as the filament cools. However, because the x-ray tube is in operation (i.e., high-voltage is applied), filament cooling is actually much faster than it would be if the tube were idle due to depletion of "hot" electrons from the electron cloud surrounding the filament.

(4) Ideally, the desired low x-ray tube flux output (or radiation dose) desired for fluoroscopic examination would be produced by operating the tube at a "normal" high voltage and a relatively low x-ray tube current. Because the x-ray tube filament cannot be instantaneously cooled to reduce the tube current to a preferred value, the desired tube output is instead achieved by immediately reducing the high voltage (which can be almost instantaneously controlled) to a level which produces the same desired x-ray tube output at the relatively high initial current. The imaging system calculates the appropriate x-ray tube high voltage based, in part, on known values of the x-ray tube current and high voltage which were used to perform the immediately-previous radiographic exposure.

(5) An automatic brightness system (ABS) is used to control the output of the X-ray tube during the fluoroscopic examination while the X-ray tube filament cools and the X-ray tube current decays to a desired value for fluoroscopy. Because an x-ray tube output depends on tube current and high voltage, as the tube current falls, the high voltage must be correspondingly increased to achieve constant tube output. ABS is a known method of automatically adjusting the X-ray tube output to provide consistent brightness in the image displayed on an image-intensifier screen. ABS systems typically operate by controlling x-ray tube high voltage, but may control other parameters. Preferably, the ABS of the inventive imaging system controls x-ray tube high voltage. Thus, throughout the fluoroscopic examination, and in particular while the tube current is changing, the ABS operates to automatically adjust the high voltage as required to produce an appropriate tube output for fluoroscopy. Eventually, the x-ray tube filament will have cooled such that the tube current reaches the preferred value for fluoroscopic examination; at that time, the anode voltage will have been automatically increased to a "normal" value for fluoroscopy due to action of the ABS.

According to another aspect of the present invention, the pulse repetition rate used for pulsed fluoroscopy is automatically selected by the system using movement-related information, such as movement detected in an x-ray (fluoroscopic) or optical image, operator requests for movement of the patient or imaging system, or knowledge or observation of characteristics of an examination. A low pulse repetition rate may be generally used. Since the patient under examination is typically resting on a movable table, the movements of which are either controlled by or monitored by the imaging system, the system may automatically switch to a higher pulse repetition rate whenever the system causes or detects a request for (or attempt to produce) movement of the patient table or imaging system. In addition, the system may analyze the fluoroscopic image, or an optical (visible- or infra-red light) image of the patient, or aspects thereof, and automatically switch to a higher pulse repetition rate whenever the image is observed to have changed in a significant way. For example, the imaging system may switch to a higher pulse repetition rate when it is apparent from the image that motion has occurred or a dye or contrast medium has arrived in a window of interest. In addition, change in pulse rate may be proportional to the rate of movement. Other imaging system parameters may also be changed in response to movement-related information.

Automatic control of the fluoroscopic pulse rate makes it substantially easier for the examiner to conduct the examination at the lowest pulse rate appropriate for the current examination conditions, thereby resulting in a lower dose to both patient and examiner.

According to another aspect of the invention, methods and apparatus are provided for automatically detecting motion in a video image acquired by a diagnostic imaging system using x-rays or an optical camera. The motion detection system is particularly suited to applications in medical diagnostic imaging.

In first motion detection mode, the full field (i.e. the entire extent) of the acquired image is used for motion detection. The user selects an image variation threshold level. A baseline value for a selected characteristic of the image is initially determined. If the value of the selected characteristic later changes by an amount greater than the user-selected image variation threshold level, motion detection logic determines that motion has occurred.

In a second motion detection mode, a single user-selected window or region of the display is defined, and motion detection operates only with respect to that portion of the image. Motion detection logic operates as described above to detect motion when a change in the window exceeding a user-selected threshold occurs.

A third motion detection mode is directed to detect the progress of a dye or contrast agent through the image in an expected direction. First and second user-selected windows are defined, corresponding to initial and final expected positions of the contrast agent respectively. Motion detection logic operates as described above to detect initial presence of the contrast agent when a change in the first window exceeding a user-selected threshold occurs. When the initial presence of the contrast agent is detected, the imaging system may take certain actions to improve the diagnostic image and to eliminate motion artifacts. For example, the system may increase the fluoroscopic pulse repetition rate, disable frame integration, and enable edge enhancement. The imaging system now monitors the second window for a change in the image exceeding a second user-selected threshold. If a change which exceeds the threshold is detected, the contrast agent is determined to have reached a final desired position, and a radiographic examination may be triggered. Alternatively, a comparison may be made between characteristics of the two windows to reject common-mode changes in the image.

According to a further aspect of the invention, the inventive imaging system may use movement-related information obtained from the above-described video motion detector, or from other sources, to control the operation of the imaging system. For example, the imaging system may respond to movement-related information to initiate a radiographic exposure or advance to the next step of a programmed sequence of interspersed radiographic and fluoroscopic exposures.

A "stepping" mode of discretely positioning the imaging system in a sequence of radiographic exposures is provided. The system positions the imaging system to a predefined patient location, and initiates a fluoroscopic examination. When the system observes that the contrast agent has reached the end of the viewing area, a radiographic exposure is taken, and the system is moved to the next predefined patient location.

A "follow" mode of continuously positioning the imaging system is also provided in which the imaging system position follows the contrast agent as it moves through the patient, thereby maintaining the contrast agent (or a detectable mass or leading edge thereof) within the fluoroscopic viewing area. The imaging system makes radiographic exposures at predetermined positions.

Automatic control of certain imaging system functions based on detected patient motion can provide improved examination results because the time required to electronically detect the movement and initiate the desired function can be much smaller than that required when observation by a human operator is involved. Further, although the attention of a human operator may stray, the automatic system remains constantly vigilant, and therefore less likely to miss an movement of interest.

In addition to improving examination quality, the automatic motion detection may result in the delivery of a reduced total X-ray dose to both the patient and the examiner. If an event of interest is missed, either the patient must be re-examined, or the patient must be instructed to perform the movement or event again. In either case, missing the event results in an increased dose. By avoiding missed events, the automatic motion detection of the present invention can result in a lower x-ray dose.

BRIEF DESCRIPTION OF THE DRAWINGS

These and other features of this invention will be best understood by reference to the following detailed description of a preferred embodiment of the invention, taken in conjunction with the accompanying drawings, in which.

DETAILED DESCRIPTION OF THE PREFERRED EMBODIMENT

A preferred embodiment 100 of a Radiographic/Fluoroscopic diagnostic imaging system which provides higher-quality patient examinations, reduced patient dose, and faster transitions between radiographic and fluoroscopic modes, and which is constructed according to the present invention is shown generally in FIGS. 1–9. The term "imaging system" as used herein to refer to the invention denotes a versatile suite or combination of mechanical, electrical, and control components, which are located in substantial proximity and which function in a coordinated fashion to perform a variety of radiographic, fluoroscopic, and optionally tomographic examinations as selected by an operator.

Because medical imaging equipment requires structural support and generates penetrating radiation, in commercial applications it is often enclosed in an examination room having sturdy wall, ceiling, and floor structures constructed of a radiation shielding material, and this discussion of the preferred embodiment of the invention assumes that it will be applied in such an environment. However, the invention is not limited to application in this environment, and could be used in other environments (such as a military field hospital) if suitable structural supports and radiation shielding are provided.

In addition, although this application describes the present invention in medical imaging applications in which the images are produced using X-radiation, it will be appreciated that the present invention may also be advantageously used in applications in which images are obtained using any suitable type of penetrating radiation, or any other particle, wave, or field phenomenon.

Figure 1:
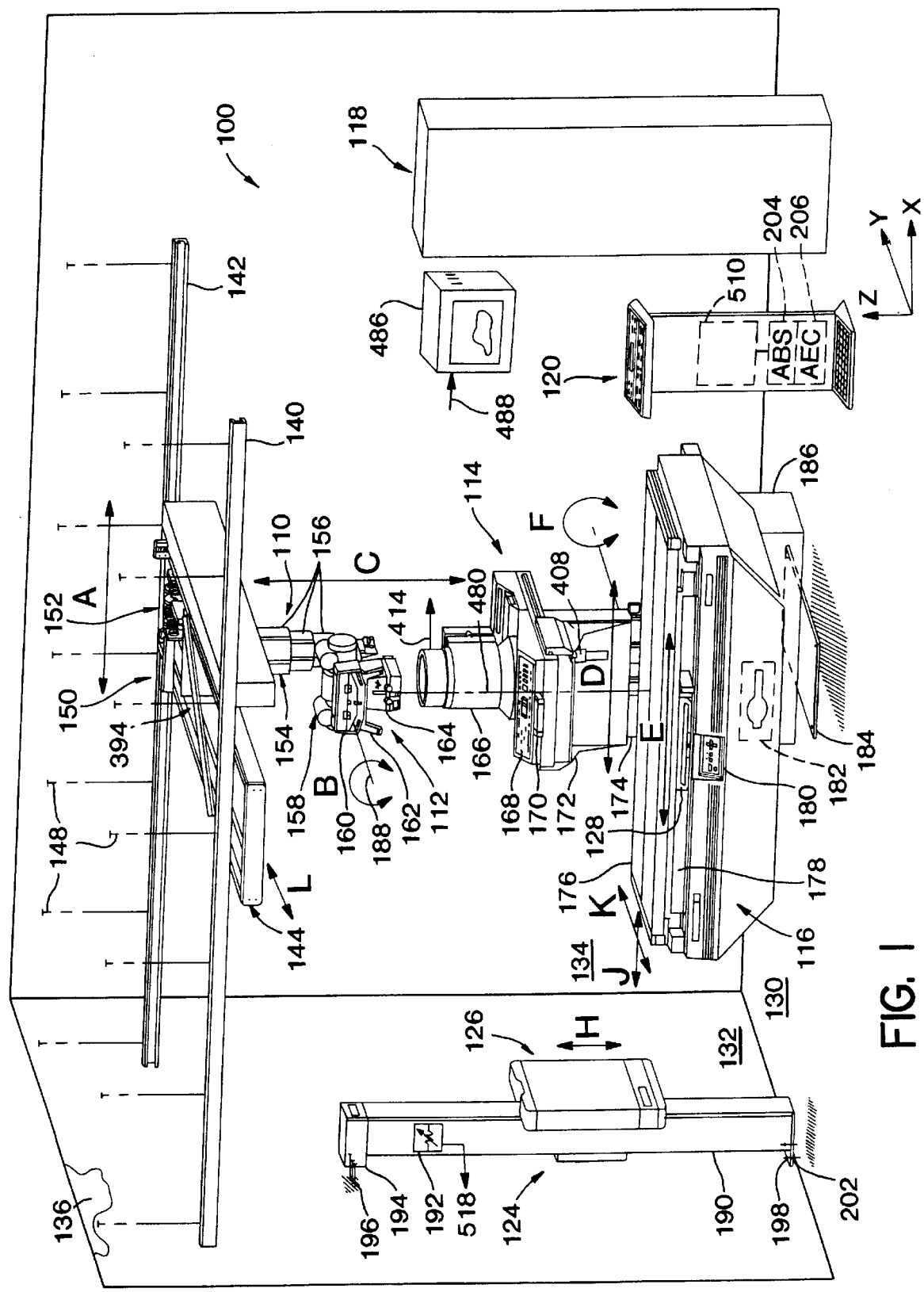
FIG. 1 is a partially exploded oblique perspective view showing the mechanical structure of a Radiographic/Fluoroscopic diagnostic imaging system, which provides an exemplary environment in conjunction with which the present invention may be implemented.
Figure 2:
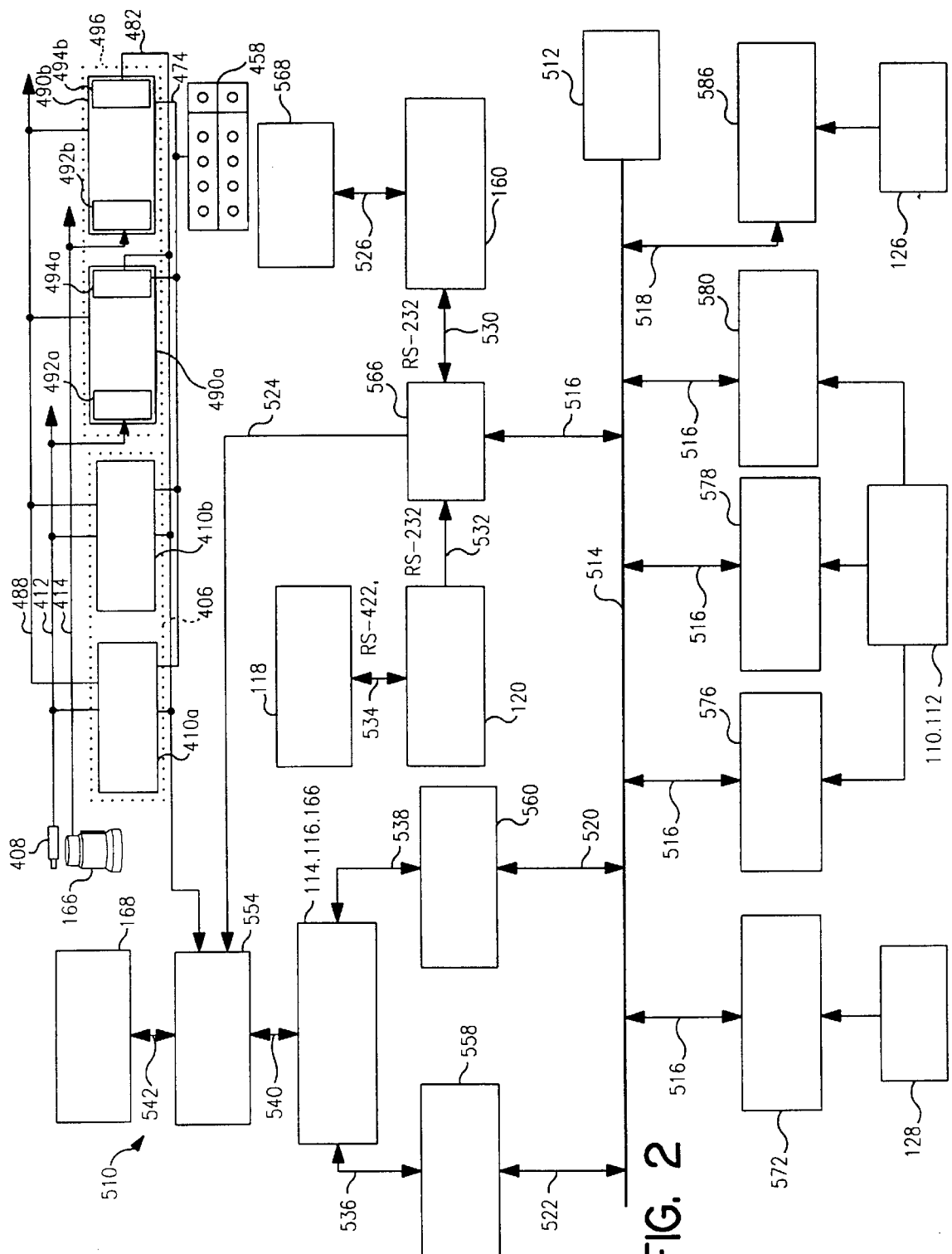
FIG. 2 is a block diagram of an exemplary control system for use in the Radiographic/Fluoroscopic diagnostic imaging system of FIG. 1 and in conjunction with which the present invention may be implemented.
Figure 5:
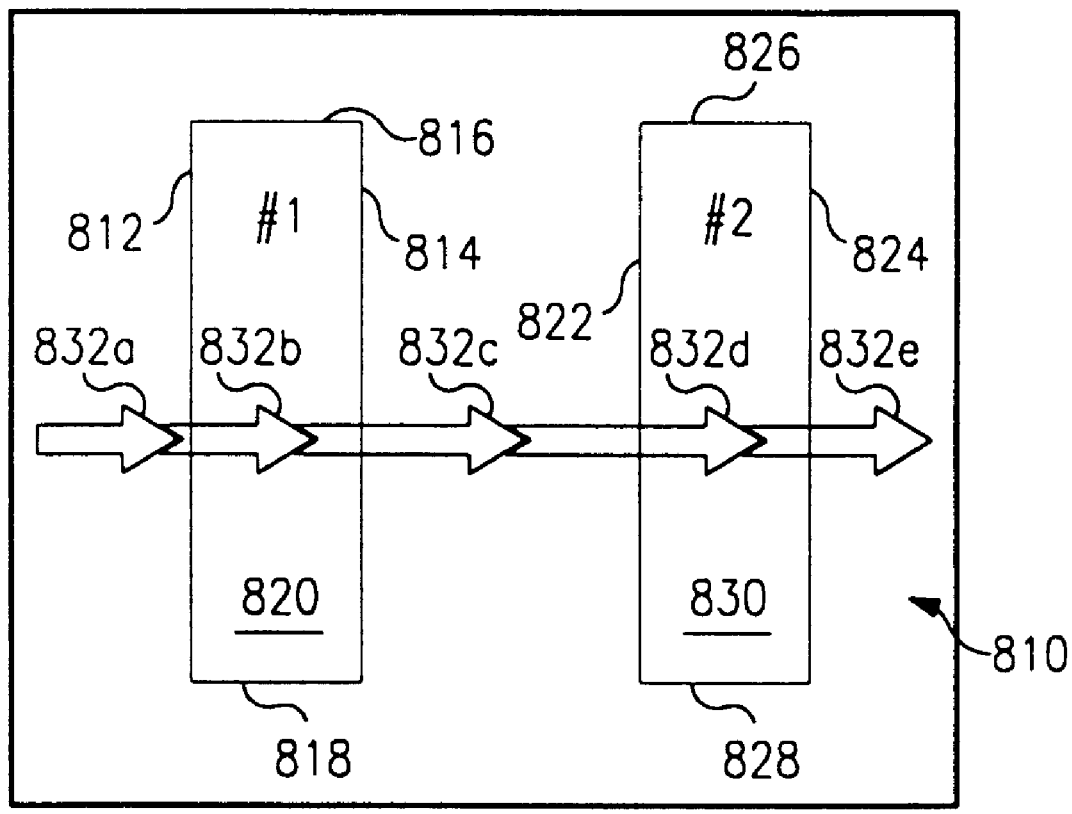
FIG. 5 is a diagram of an exemplary image display produced by the Radiographic/Fluoroscopic diagnostic imaging system of FIGS. 1–2, in which two user-defined windows are provided for detecting movement or changes in the image, and showing the progress of a contrast medium through the image.
Figure 8:
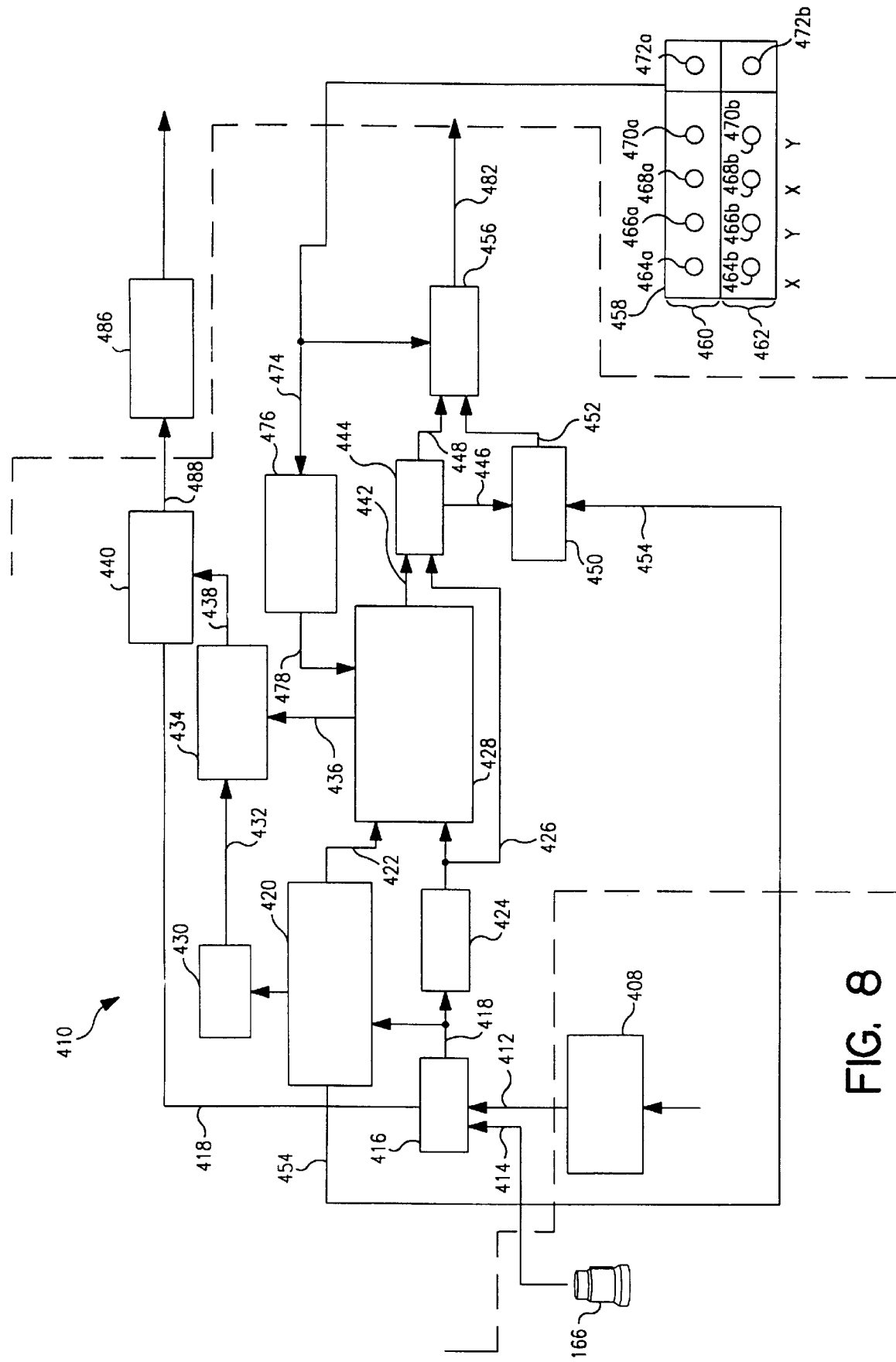
FIG. 8 is a block diagram showing the organization of a motion detection system constructed according to the invention for use in detecting motion or change in a stream of video image information.

FIG. 1 generally discloses the mechanical configuration of an exemplary imaging system 100 constructed in accordance with the present invention. FIG. 2 is a block diagram of a control system 510 for coordinating the operation of the electrical and mechanical components of the imaging system 100 of FIG. 1. FIG. 5 is a diagram of an exemplary image display produced by the imaging system showing user-defined windows of interest for automatically detecting motion or changes in the image. FIG. 8 is a block diagram of a system for automatically detecting movement or change in a stream of image information derived from the imaging system.

Figure 3A:
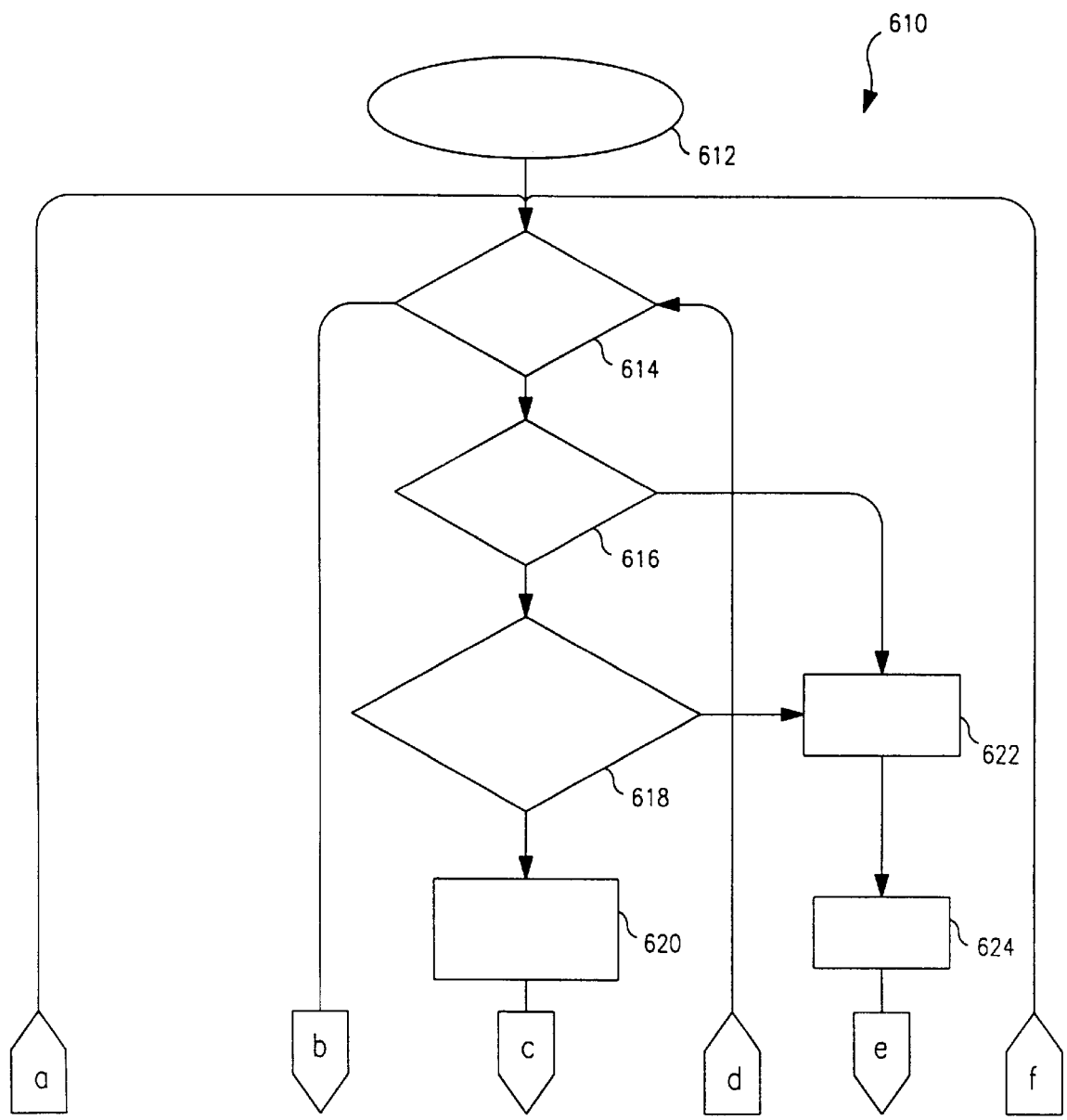
FIGS. 3a–3c comprise a flow chart illustrating an exemplary method of controlling the Radiographic/Fluoroscopic diagnostic imaging system of FIGS. 1–2 in order to provide rapid transitions between radiographic and fluoroscopic imaging modes.
Figure 3B:
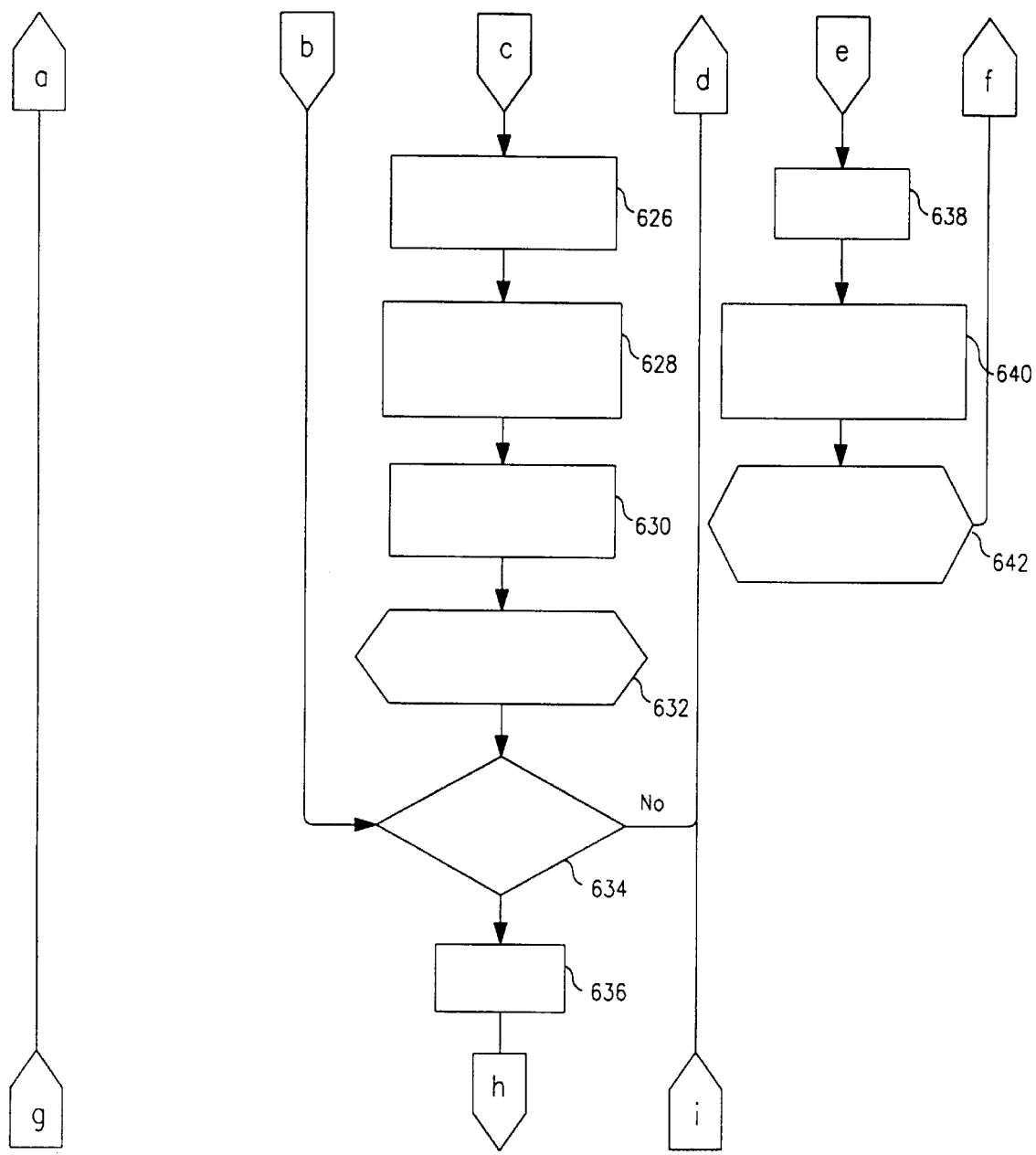
Figure 3C:
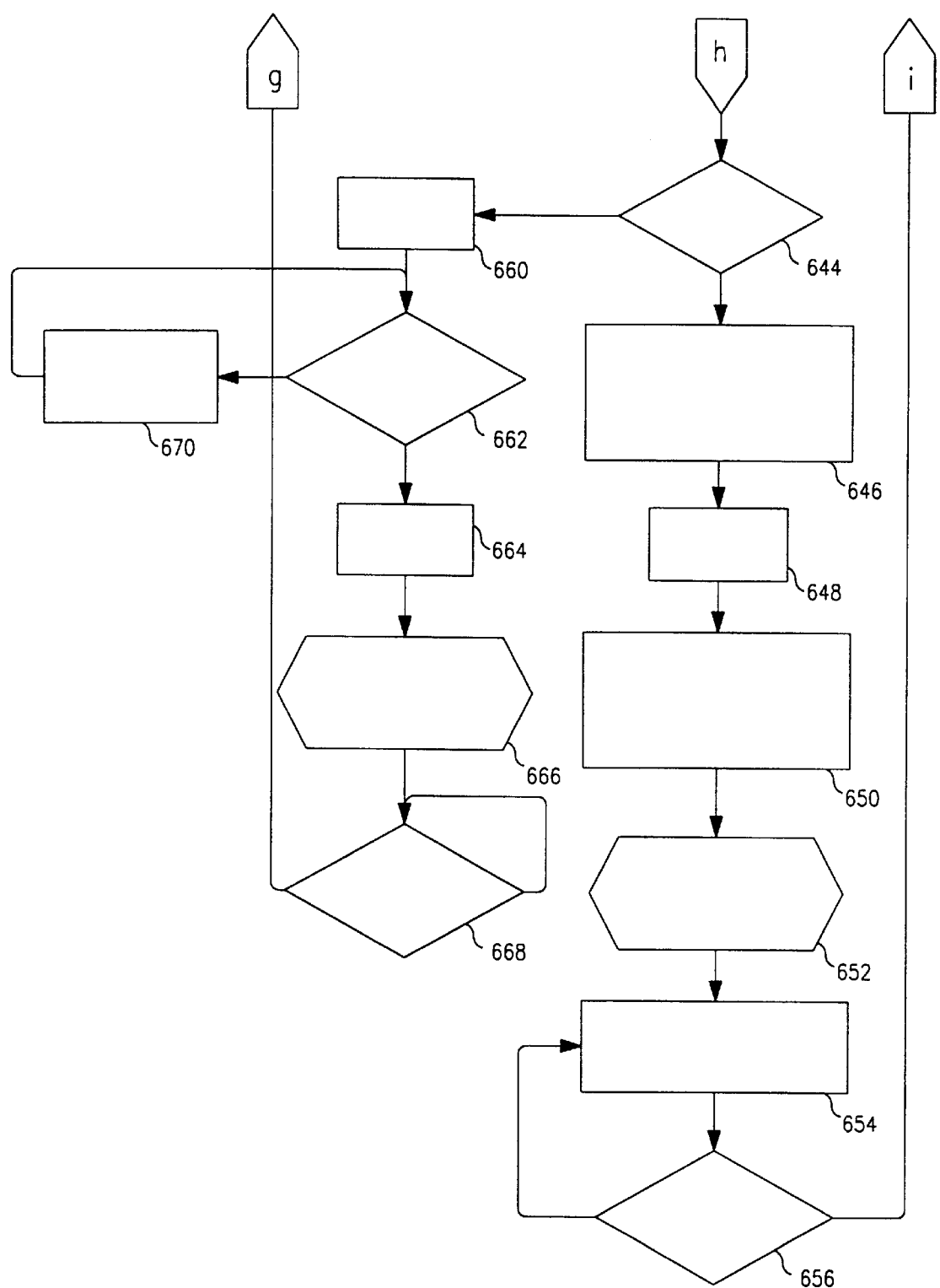
Figure 4A:
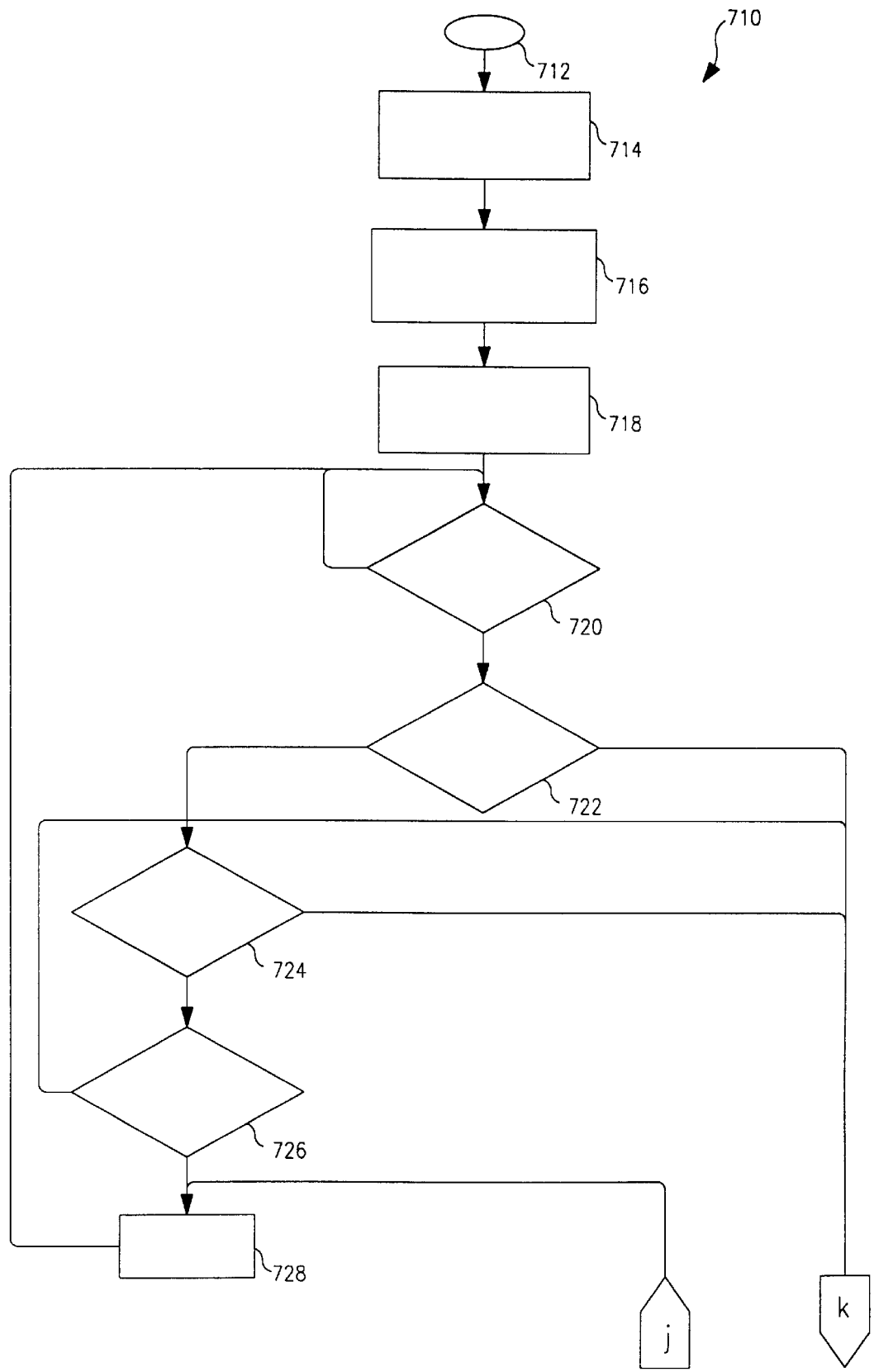
FIGS. 4a–4b comprise a flow chart illustrating an exemplary method of controlling the Radiographic/Fluoroscopic diagnostic imaging system of FIGS. 1–2 in order to reduce the X-ray dose employed while performing pulsed fluoroscopy examinations.
Figure 4B:
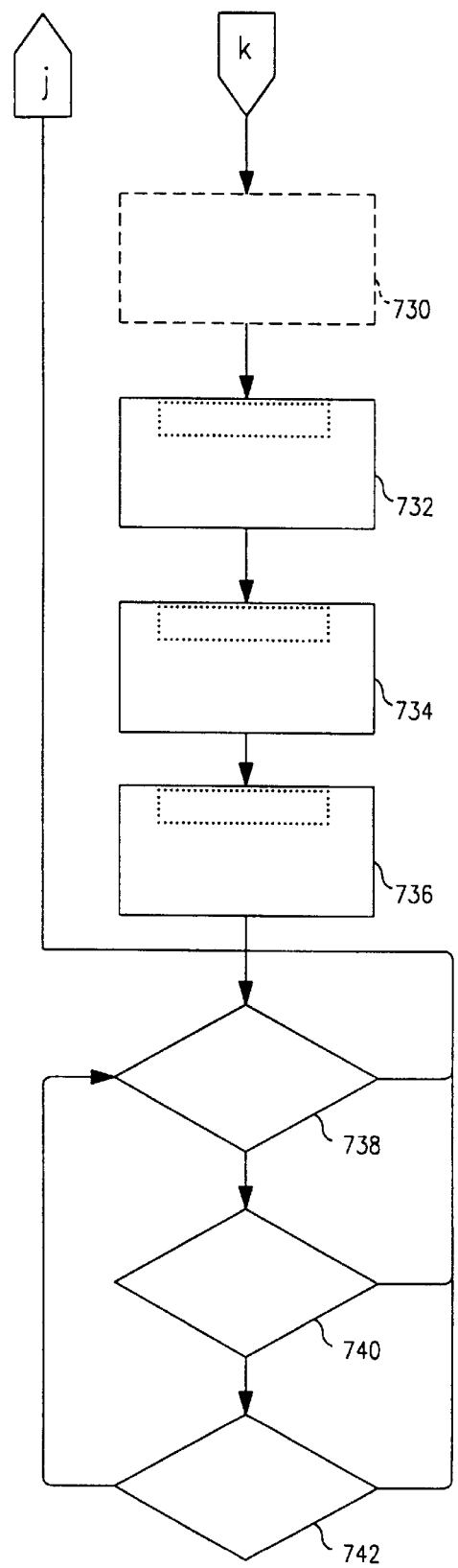
Figure 6A:
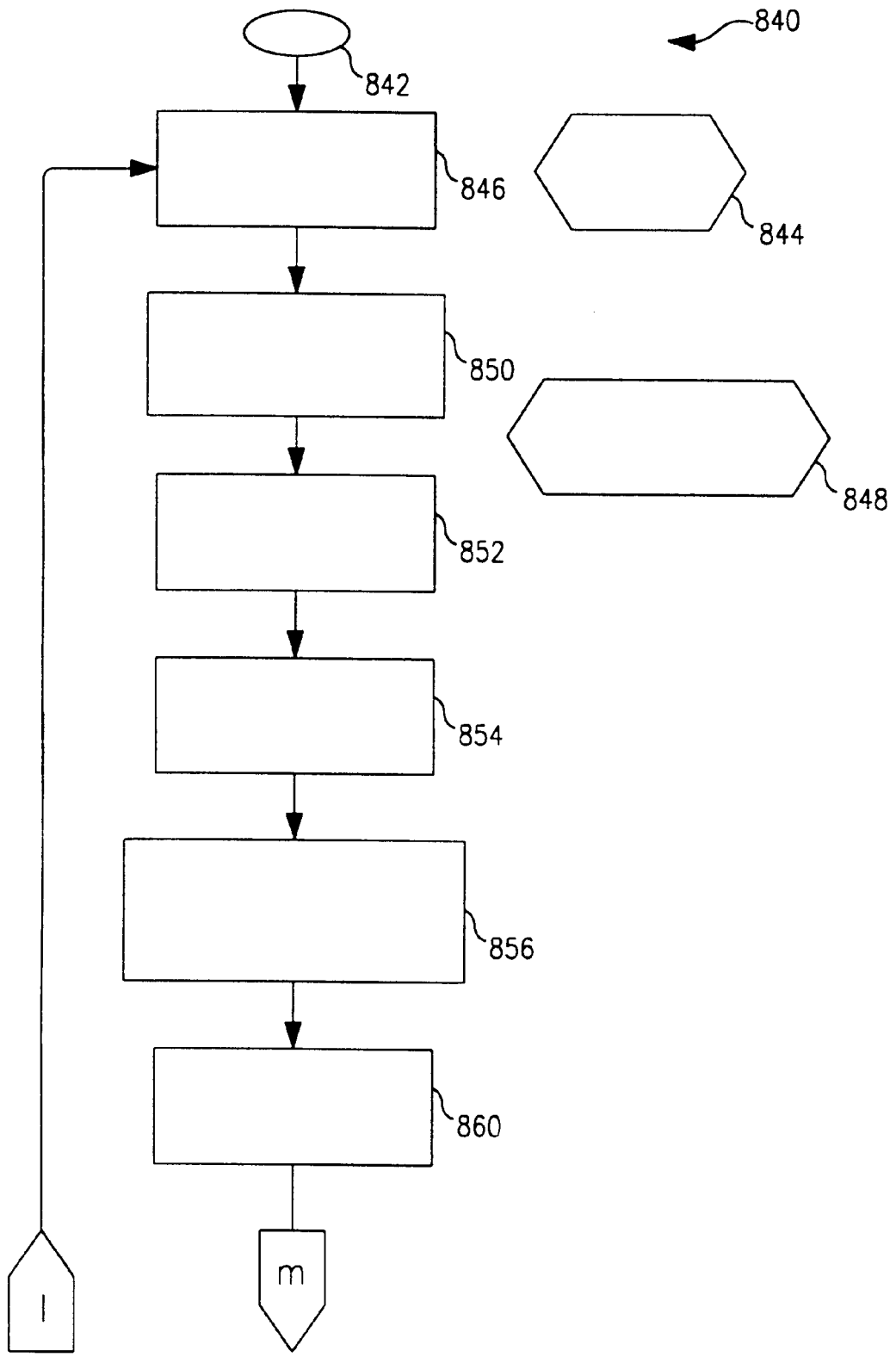
FIGS. 6a–6c comprise a flow chart illustrating an exemplary method of controlling the Radiographic/Fluoroscopic diagnostic imaging system of FIGS. 1–2 for automatically performing a predefined sequence of radiographic and fluoroscopic examinations steps in coordination with the observed movement of contrast medium through a patient.
Figure 6B:
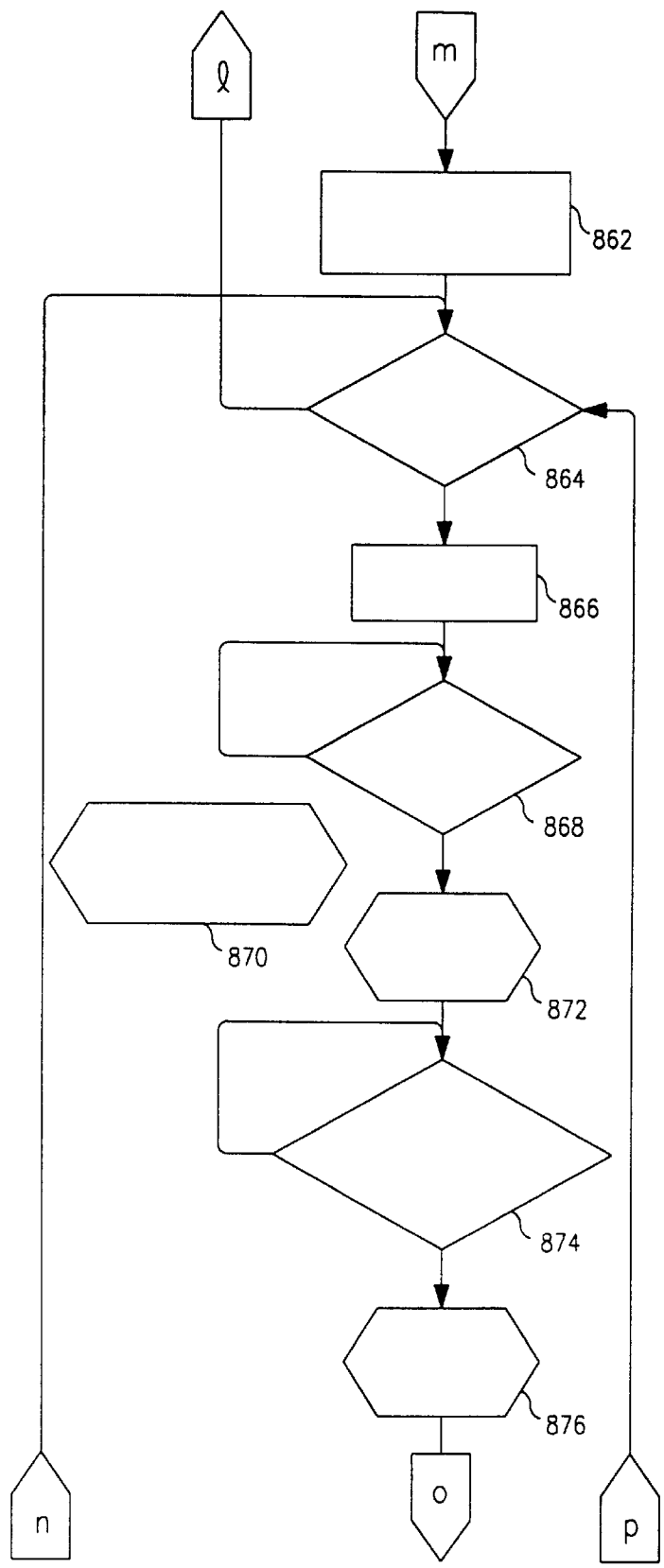
Figure 6C:
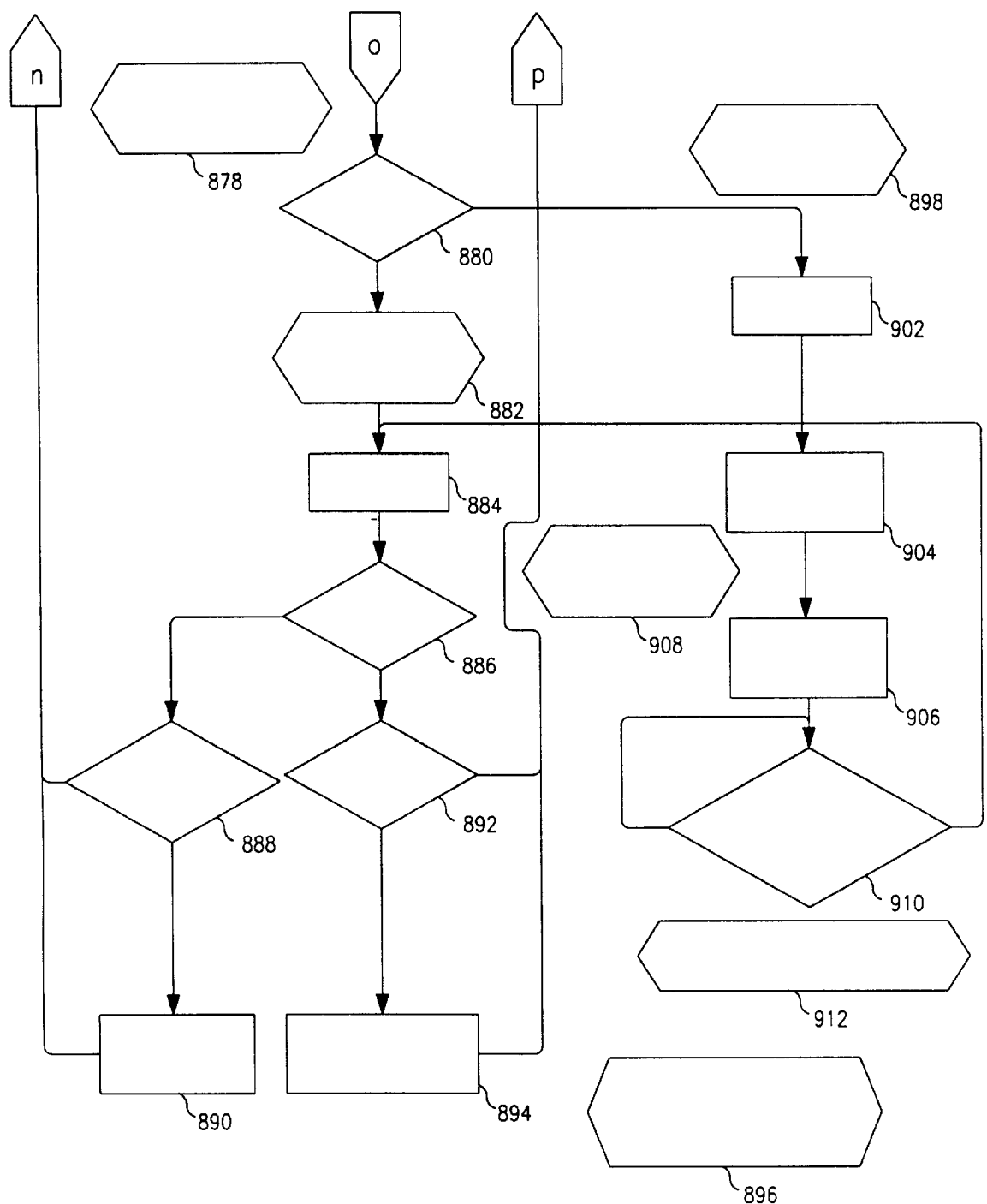

FIGS. 3a–3c are flow diagrams showing a method of controlling the imaging system 100 in order to provide rapid transitions between radiographic and fluoroscopic imaging modes. FIGS. 4a–4b are flow diagrams showing a method of controlling the imaging system to reduce the X-ray dose delivered in a pulsed fluoroscopy examination by intelligently adjusting the pulse repetition rate when movement is predicted, requested, or detected from an image. FIGS. 6a–6c are flow diagrams showing a method of controlling the imaging system to automatically perform a predefined sequence of radiographic and fluoroscopic examinations steps in coordination with the observed movement of contrast medium through a patient.

Figure 7:
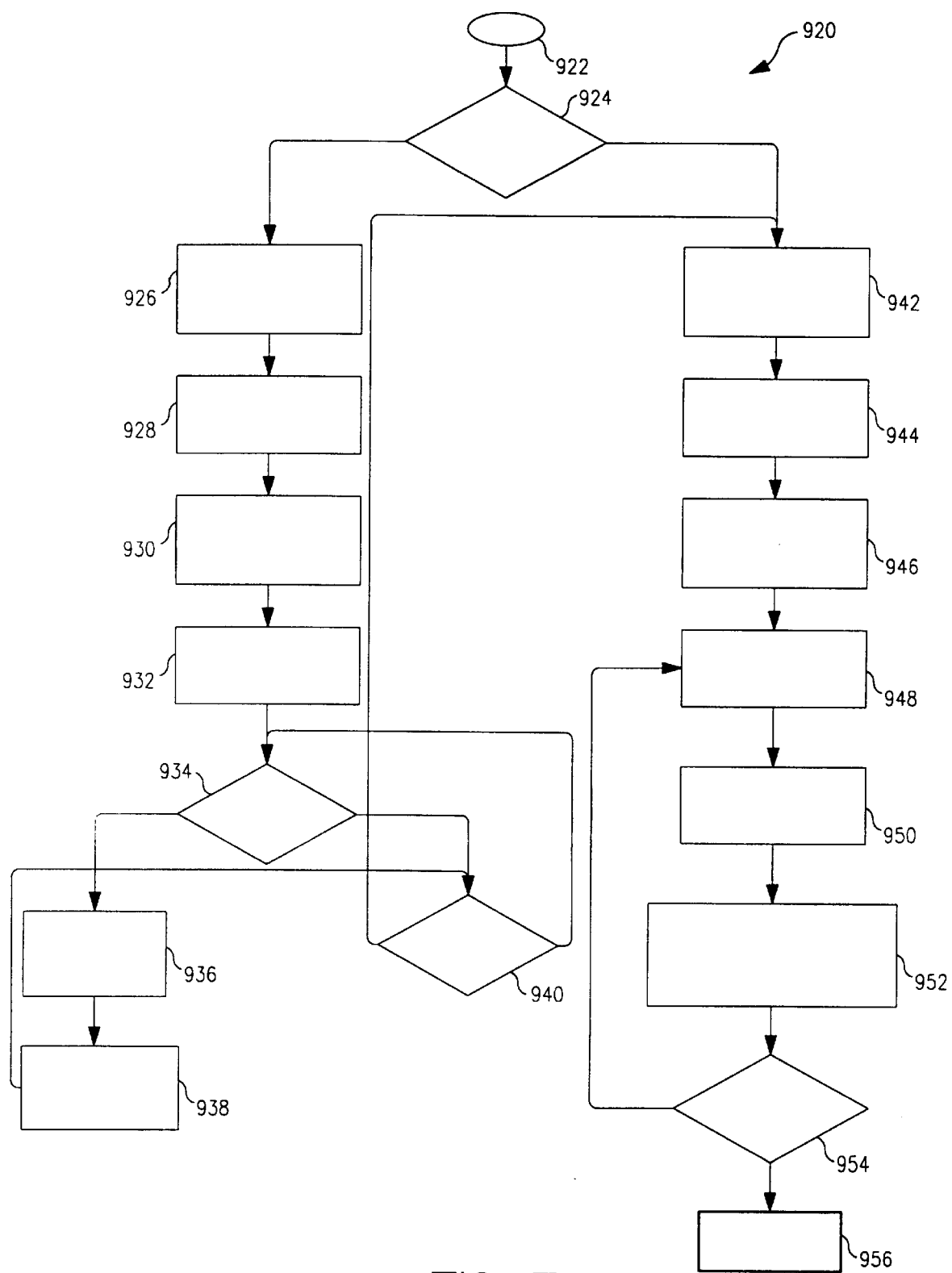
FIG. 7 is a flow chart illustrating a first exemplary method for use with the Radiographic/Fluoroscopic diagnostic imaging system of FIGS. 1–2 for detecting motion or other changes in a stream of video image information, in which the method may be performed in conjunction with programmable processor components of a general-purpose image processor.
Figure 9:
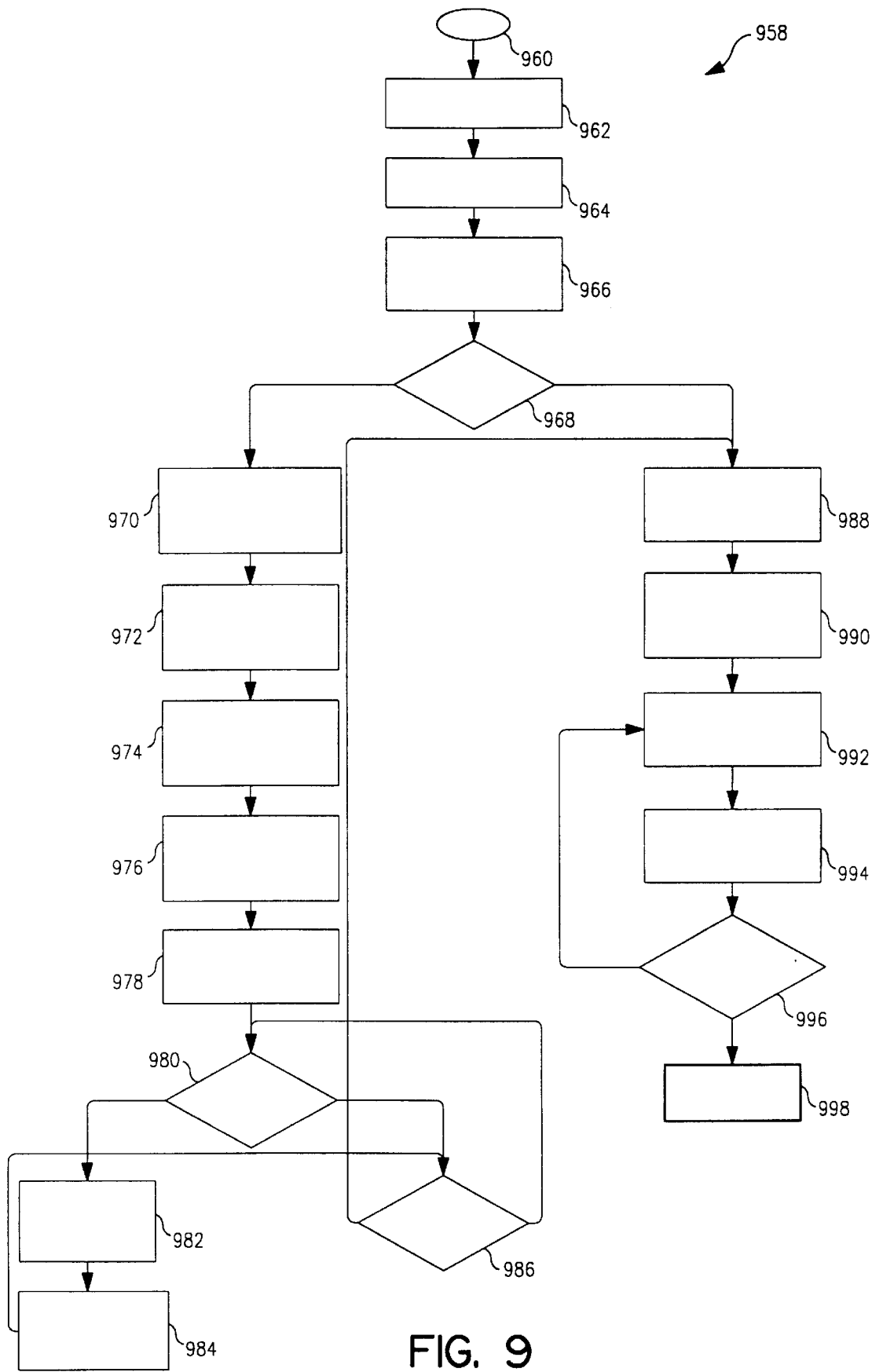
FIG. 9 is a flow chart illustrating a second exemplary method for use with the Radiographic/Fluoroscopic diagnostic imaging system of FIGS. 1–2 for detecting motion or other changes in a stream of video image information, in which the method may be performed in conjunction with the motion detection system of FIG. 8.
Figure 2:
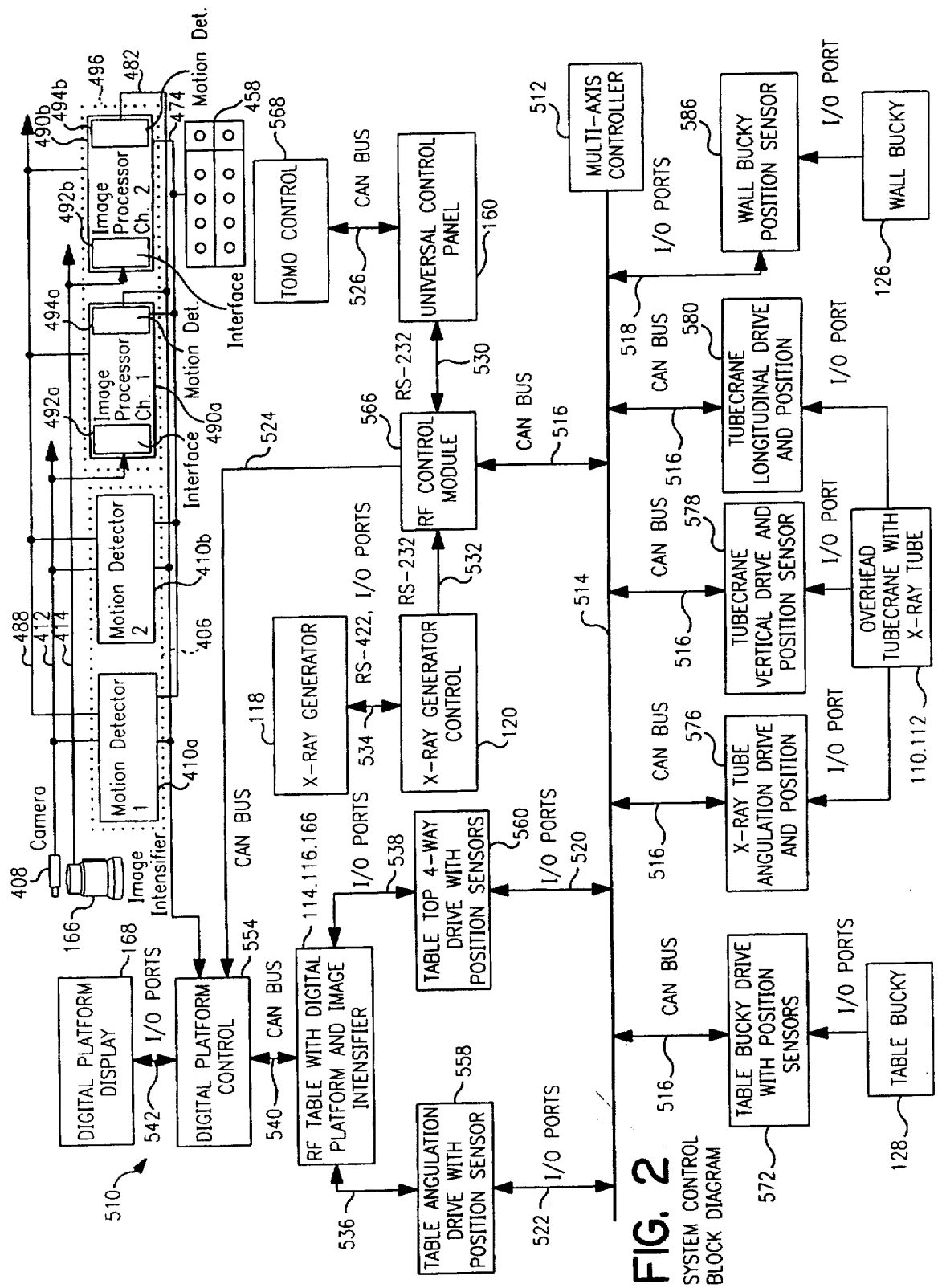
Figure 3A:
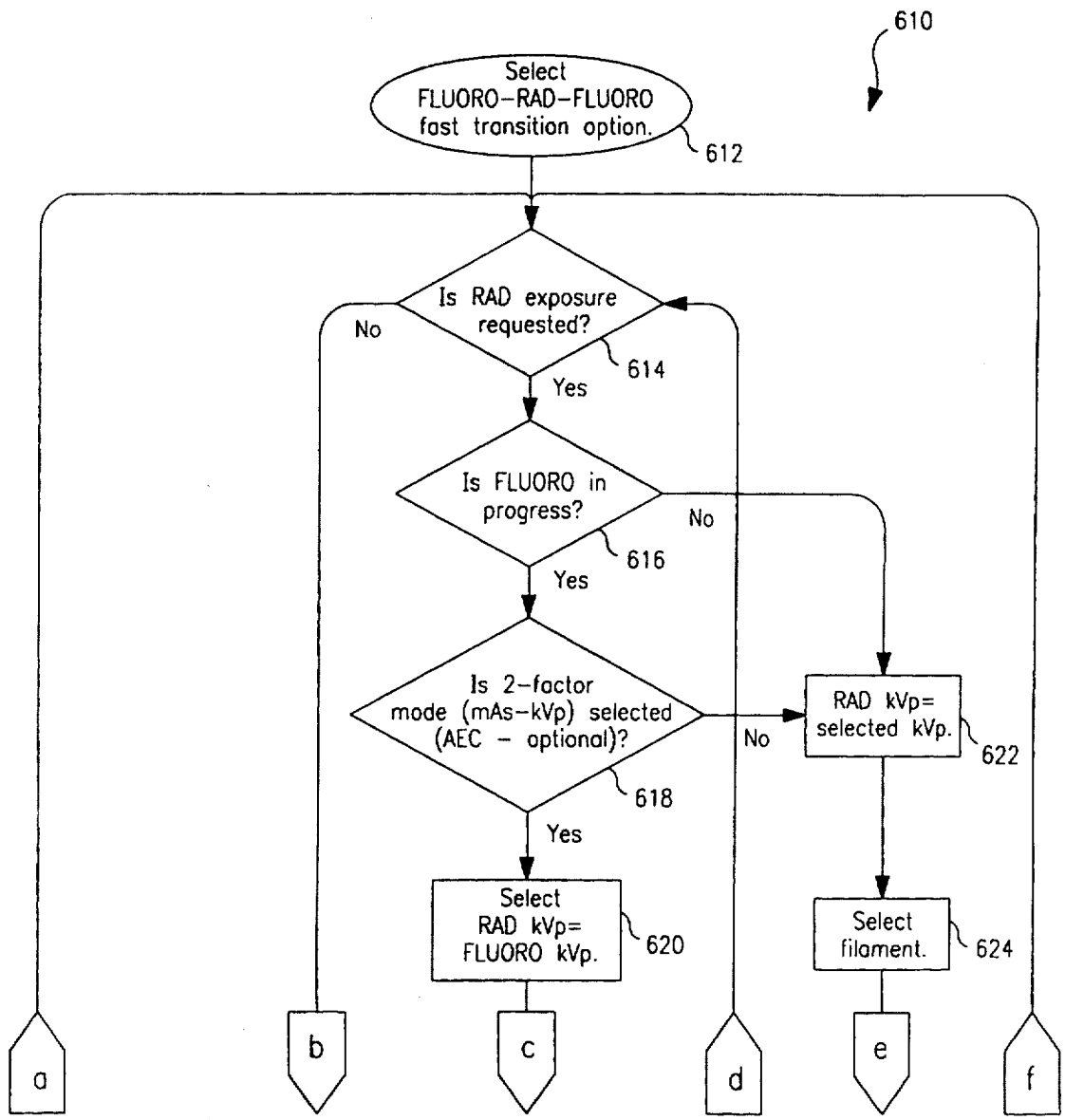
Figure 3B:
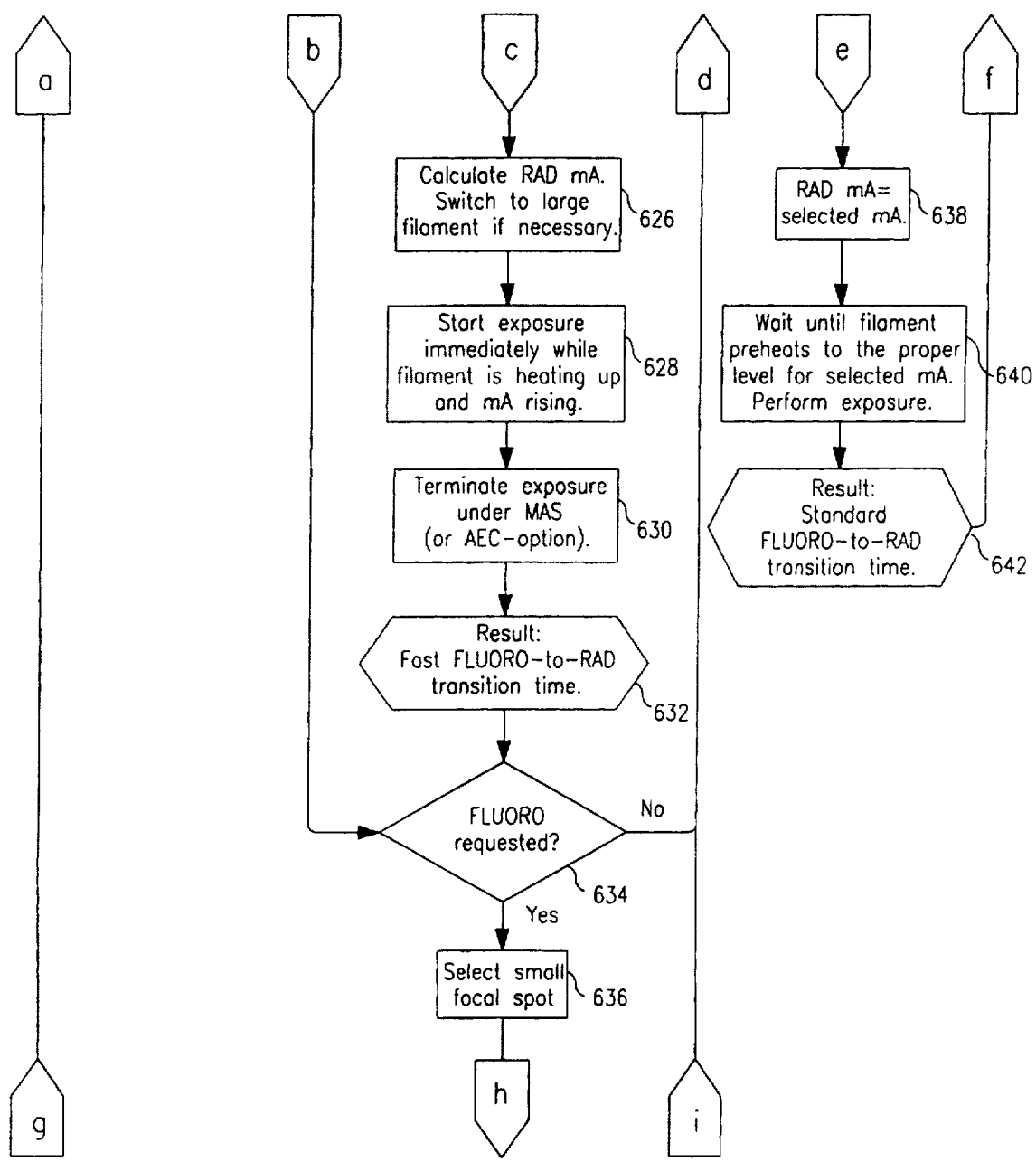
Figure 3C:
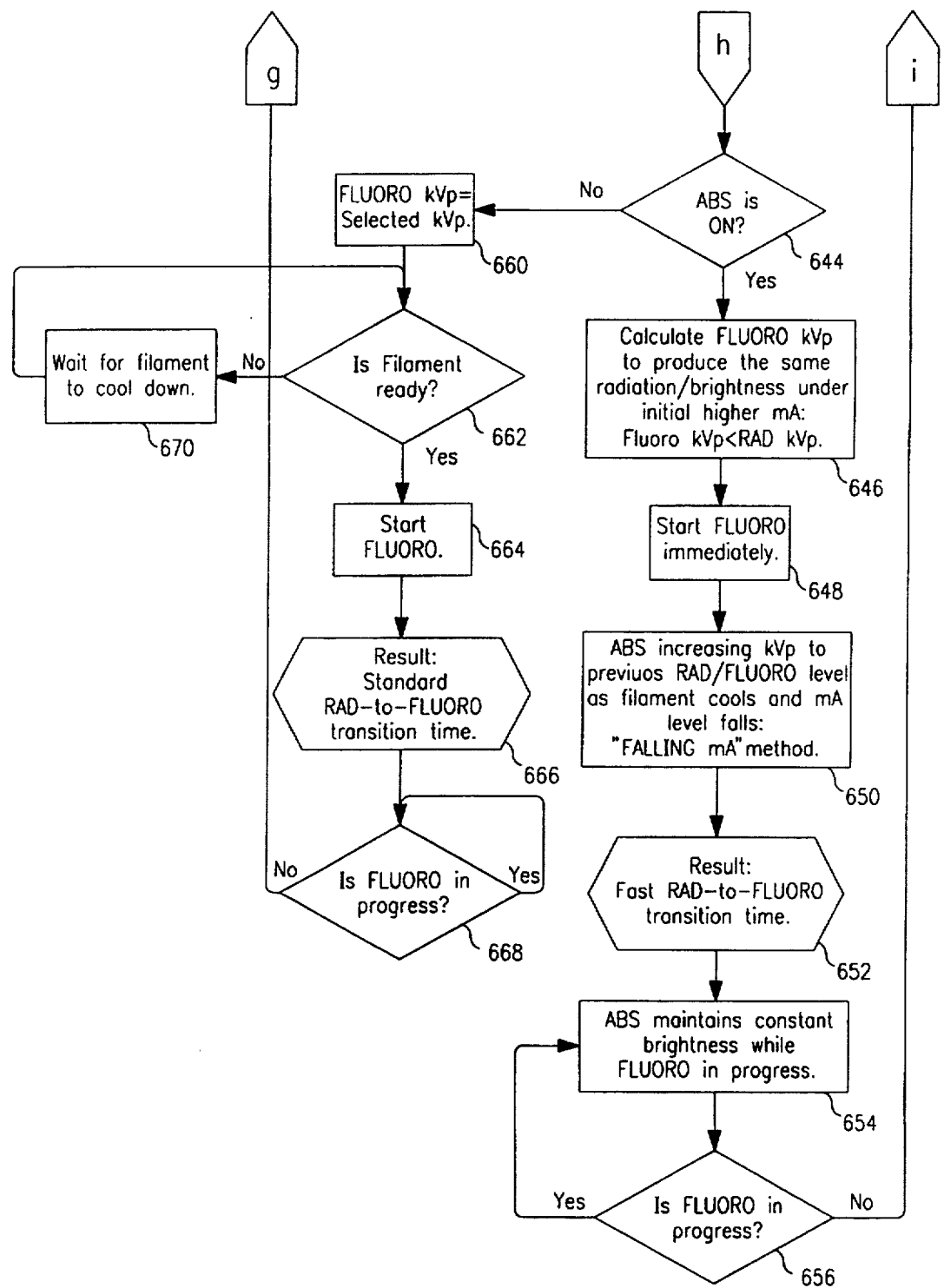
Figure 4A:
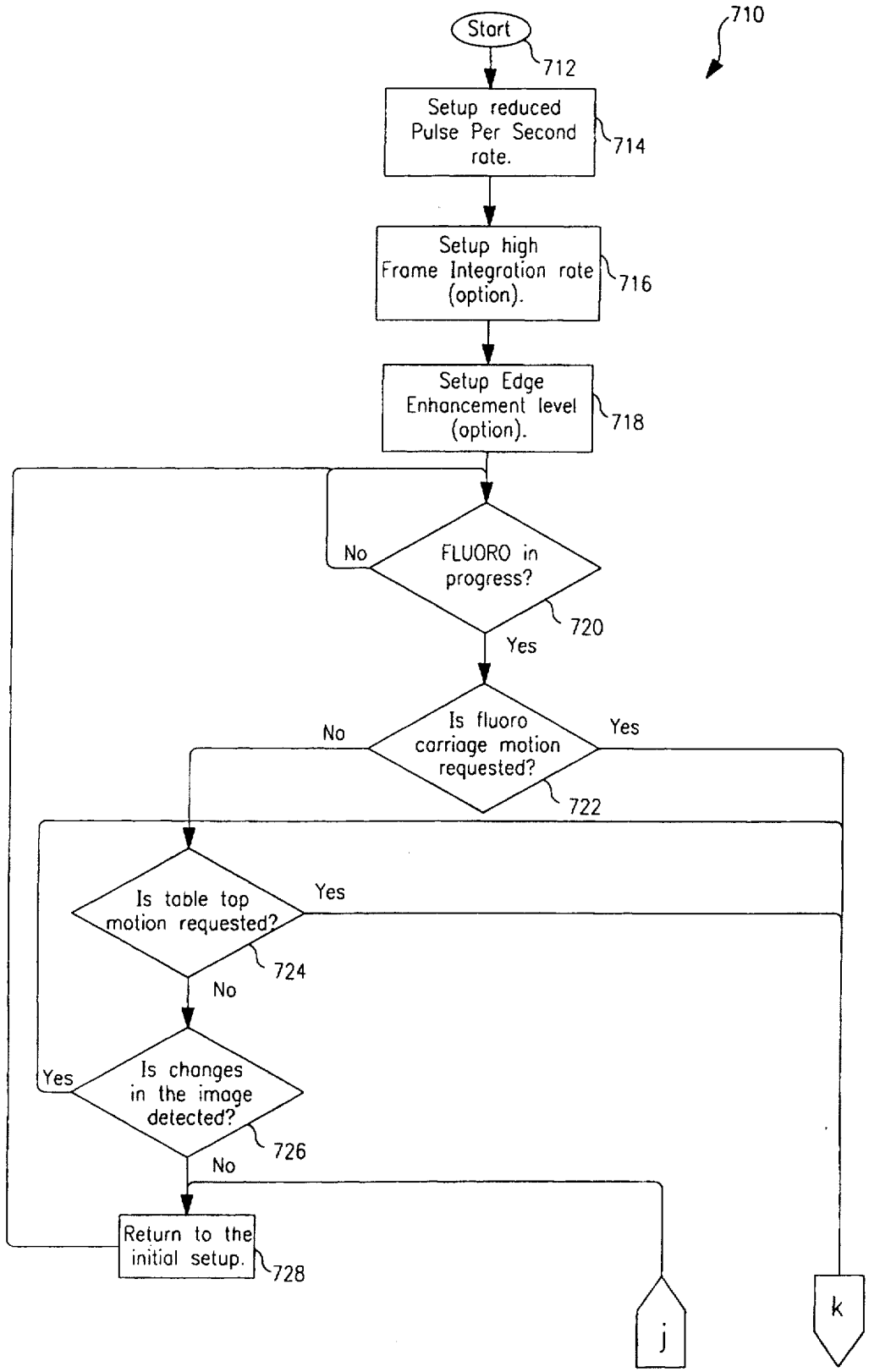
Figure 4B:
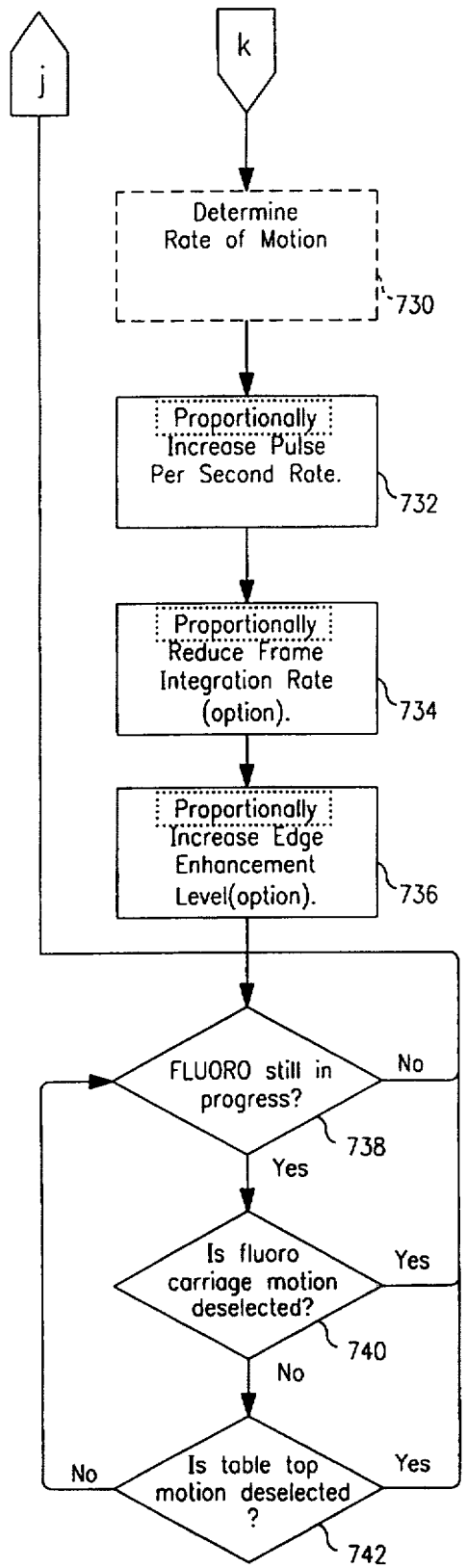
Figure 6A:
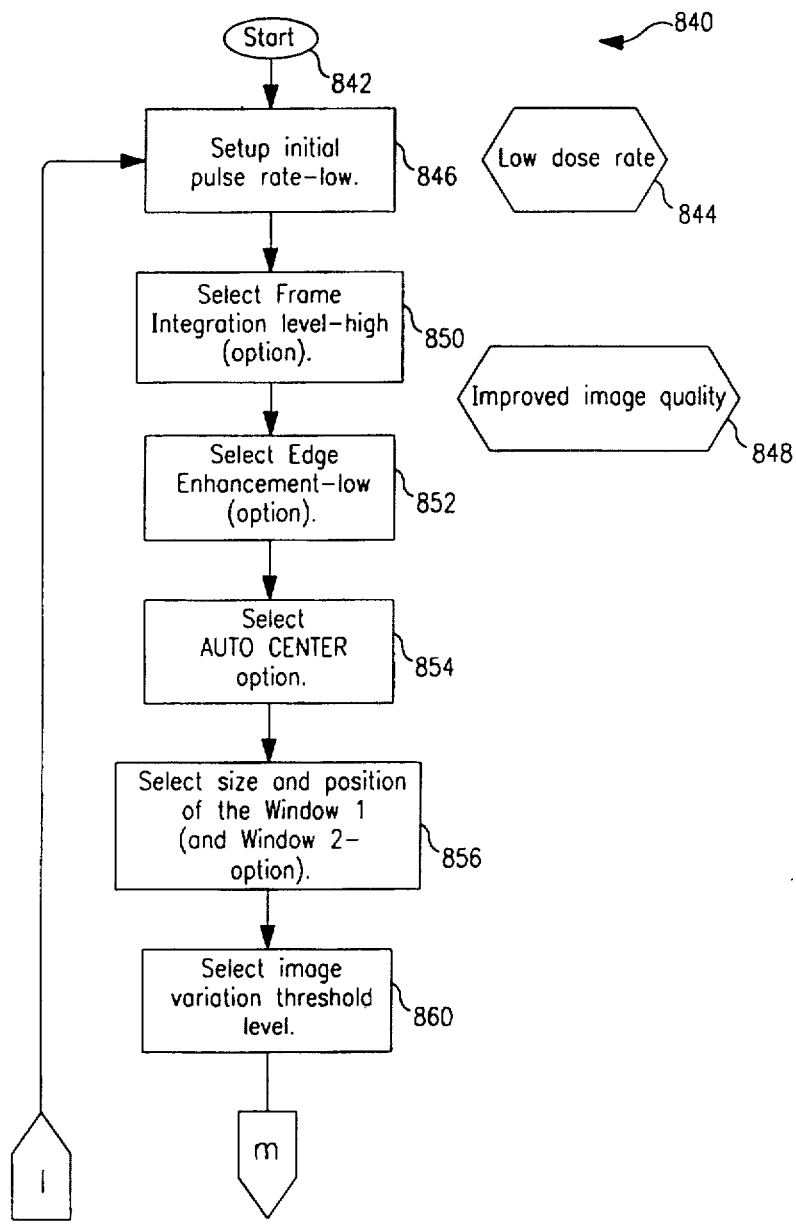
Figure 6B:
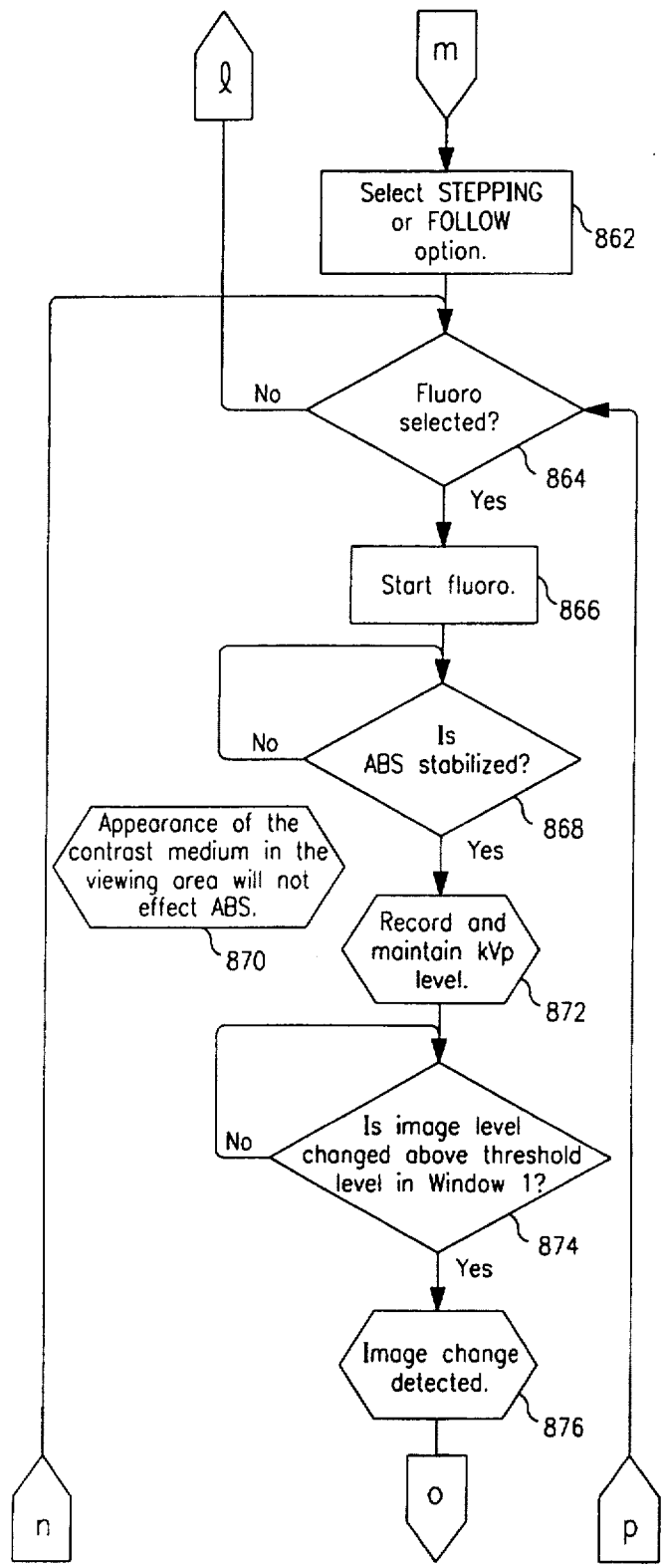
Figure 6C:
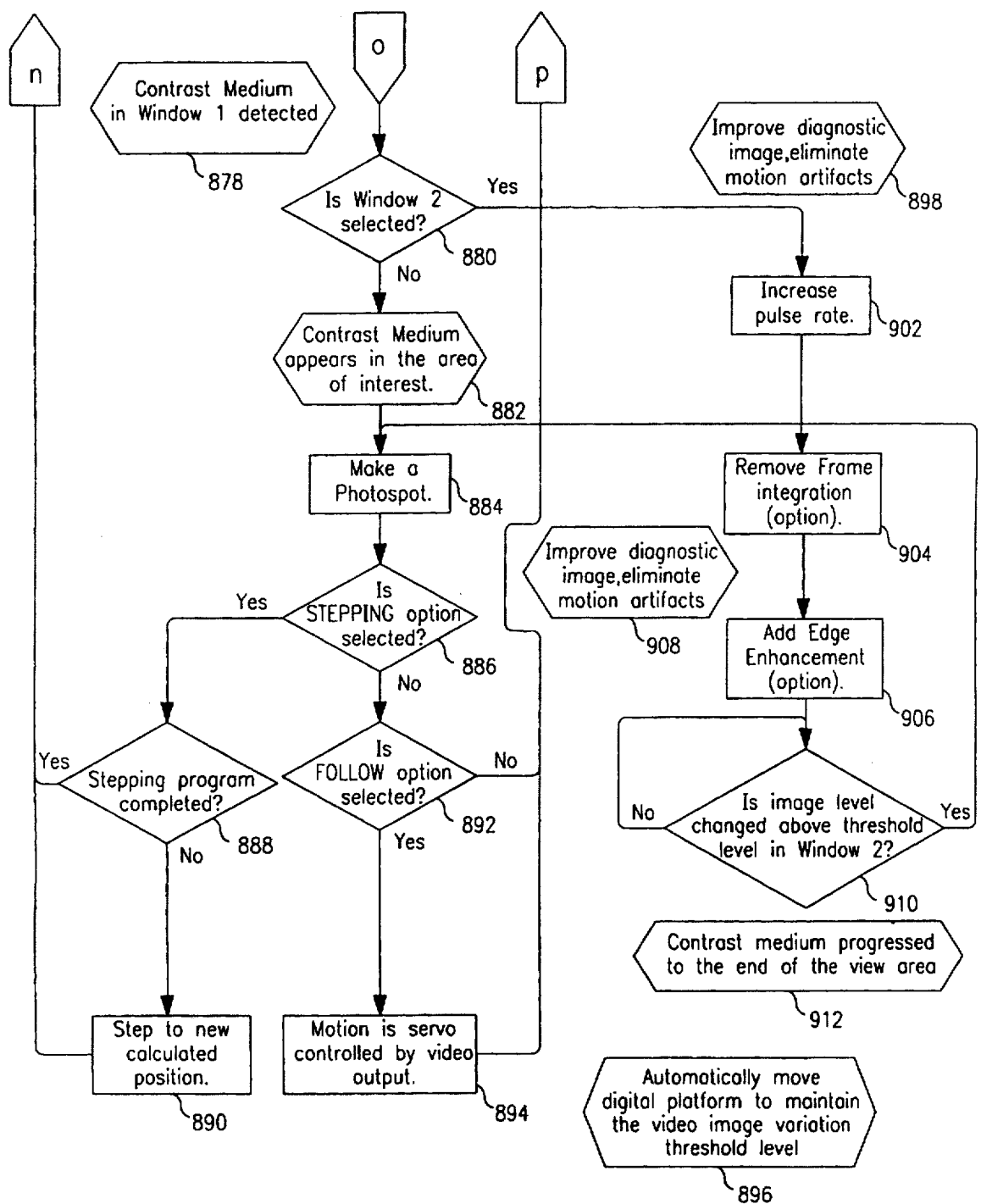
Figure 7:
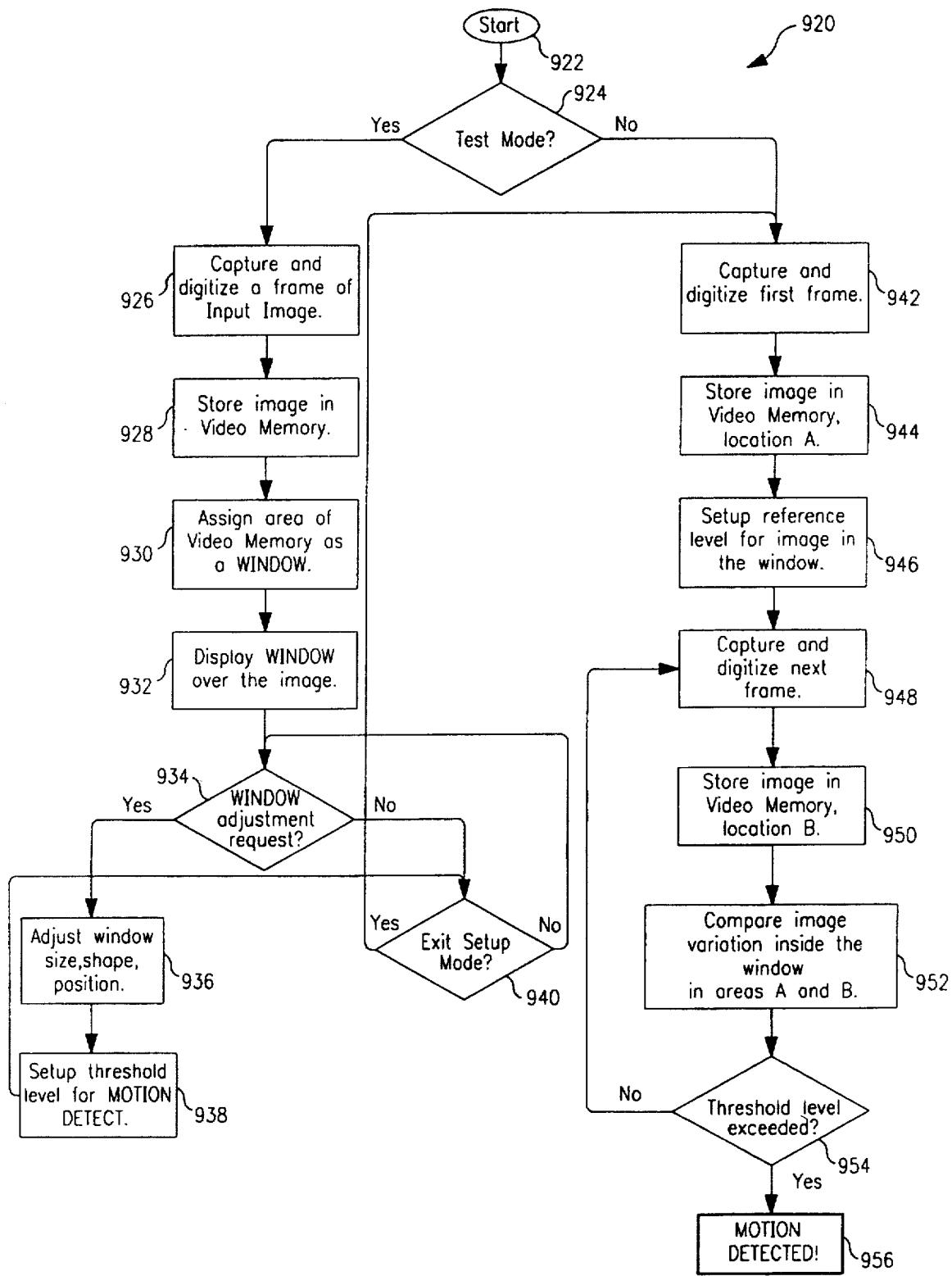
Figure 8:
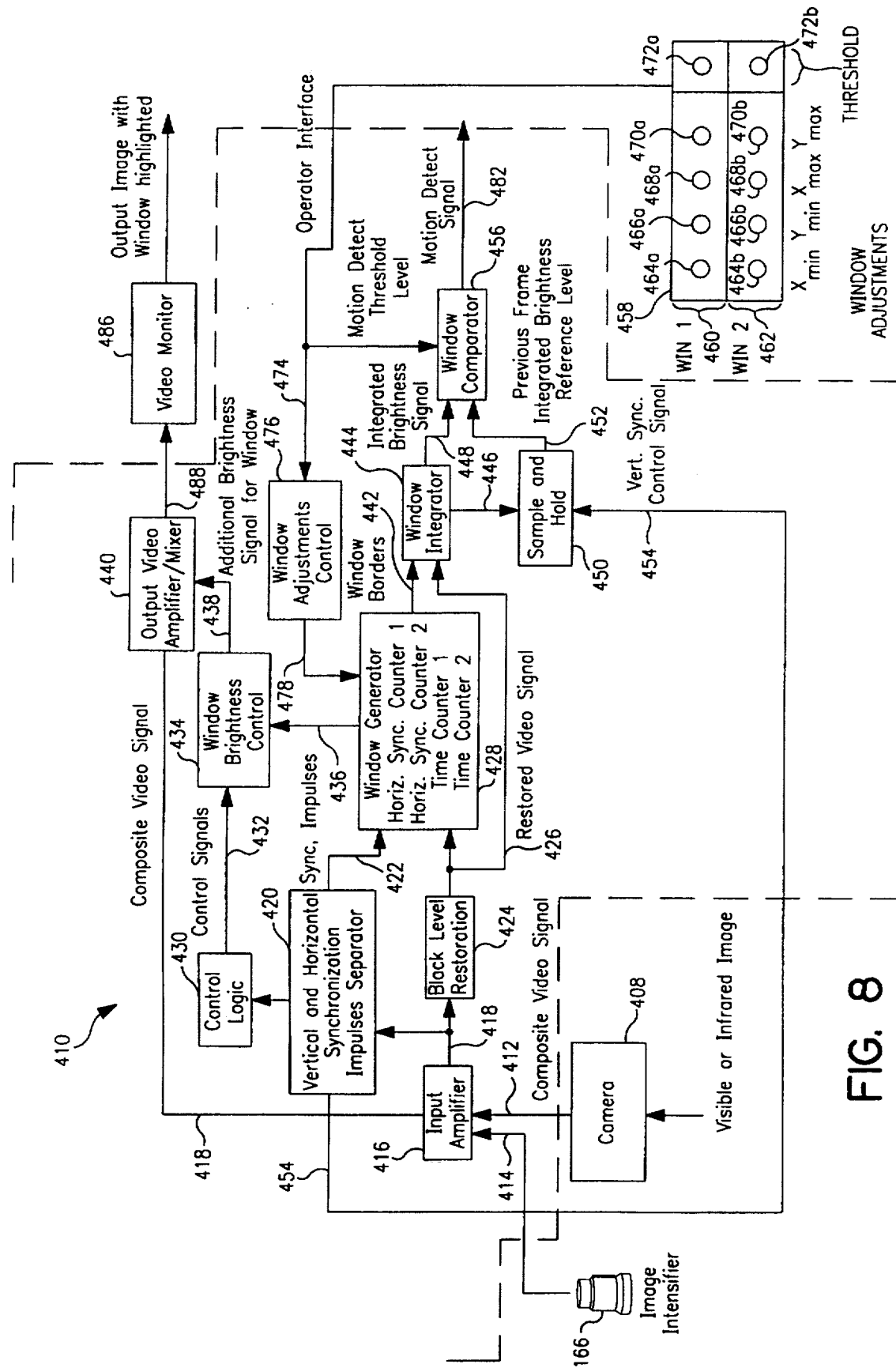
Figure 9:
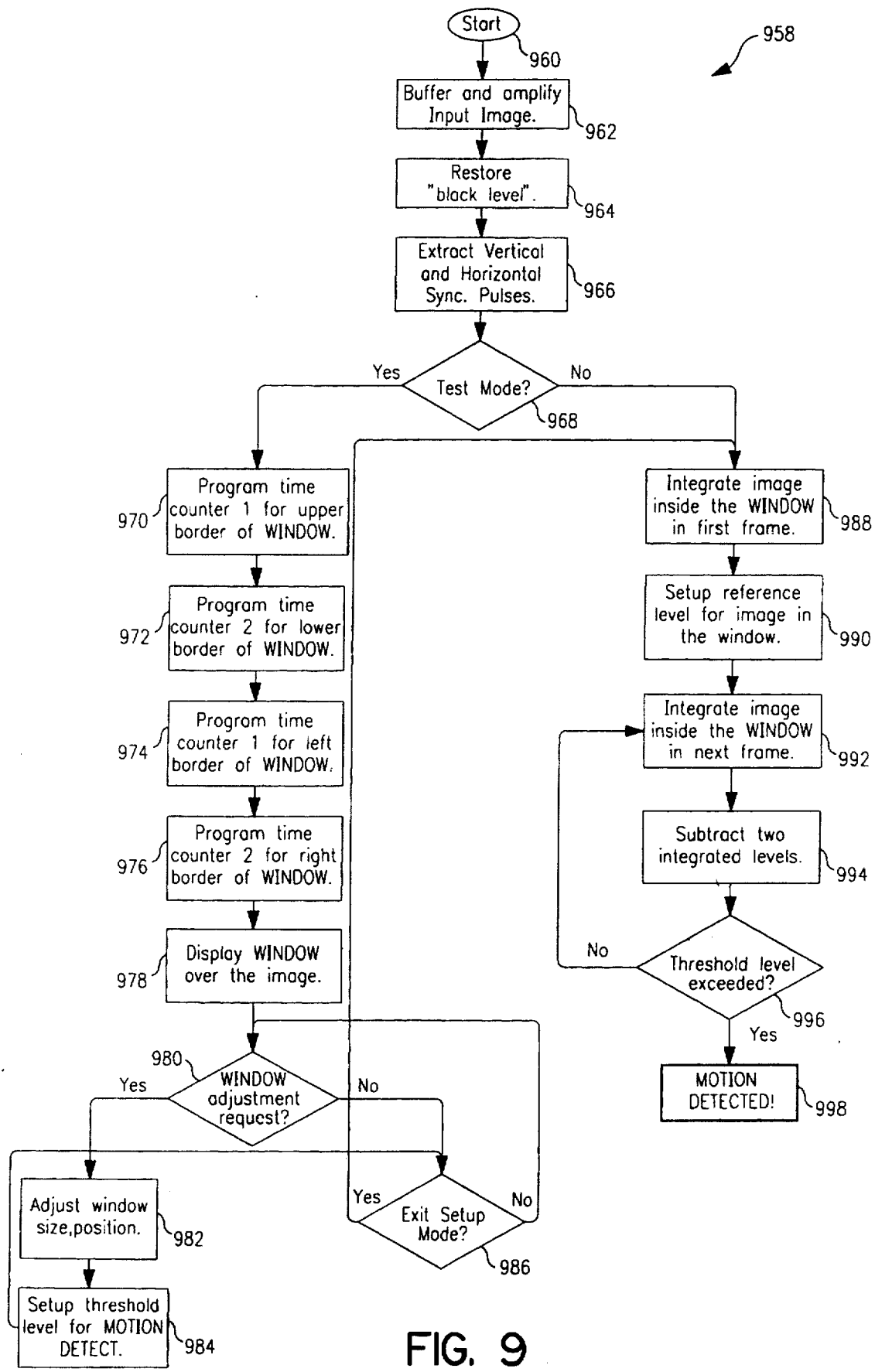

FIGS. 7 and 9 are flow diagrams showing first and second methods, respectively, for use in conjunction with the imaging system 100 for detecting motion or other changes in a stream of video image information. The method of FIG. 7 may be performed in conjunction with a programmable general-purpose image processor. The method of FIG. 9 may be performed in conjunction with the motion detection system of FIG. 8. The result from either of the motion detection methods of FIG. 7 or 9 may be used with the methods of FIGS. 4 and 6 to enable the imaging system to provide certain automatic operations in coordination with the detected movement.

The imaging system 100 shown in FIGS. 1–2 and discussed in the accompanying text forms a highly versatile Radiographic/Fluoroscopic imaging system capable of performing a wide variety of radiographic and fluoroscopic examinations. The present invention is generally directed to methods of controlling an imaging system of this type, but the invention is not limited to systems having the particular mechanical and control system configurations shown in FIGS. 1–2. Thus, the mechanical structure of the imaging system of FIGS. 1–2, and those aspects of its control system which are not directly related to implementing the present invention, should be considered an exemplary platform or environment in connection with which the present invention may be implemented. Accordingly, the mechanical structure and control system of the exemplary imaging system is discussed herein to the extent relevant to the present invention. However, the imaging system 100 may be implemented as disclosed in U.S. patent application Ser. No. 08/443,486, filed May 18, 1995, entitled "Universal Radiographic/Fluoroscopic Digital Room" (now U.S. Pat. No. 5,636,259), the disclosure of which is incorporated herein.

As best seen in FIG. 1, a preferred embodiment 100 of an imaging system constructed according to the present invention may be housed in an examination room having a floor 130, a ceiling 136, a side wall 132, a rear wall 134, and additional walls (not shown), or equivalent support members having sufficient structural strength to bear the weight of the various components of the invention.

As best seen in FIG. 1, the imaging system 100 preferably comprises several major functional components: an X-ray tube head 112 supported from the ceiling 136 by a tube crane 110; a floor-mounted examination table 116 for supporting a patient (not shown) and an imaging media cassette 128 (referred to as a "bucky") during examination; a digital imaging platform 114 supported by table 116; a wall mounted fixture 124 for supporting an additional imaging media cassette or bucky 126; an X-ray generator 118; and a main control panel 120 including a control system 510.

Certain of these components are movable in various directions in translation or rotation as indicated by the motion arrows A–H, and K–L. Some of these movements are performed manually by the operator. Other component movements are mechanically powered. The mechanically powered movements may be directed either by an operator (i.e., the movements are "power assisted"), or by the system controller in order to perform a particular imaging examination.

Tube crane assembly 110 supports the X-ray tube head 112 and provides translational movement of the X-ray tube head 112 in the longitudinal (X) direction shown by arrow A, the transverse (Y) direction shown by arrow L, and the vertical (Z) direction shown by arrow C. The tube crane assembly 110 comprises several cascaded mechanical stages, including a transverse carriage 394, a bridge 144, and a telescoping tube assembly 154, each of which permits movement of the X-ray tube head 112 in one of the aforementioned directions.

First and second spaced parallel support channels or rails 140 and 142 preferably extend longitudinally along the ceiling 136, and are attached thereto by a plurality of fastening means 148. The support rails 140 and 142 support a bridge 144, permitting longitudinal movement of the bridge 144 and everything it supports, as shown by the arrow A. The bridge 144, in turn, supports a transverse carriage 394 permitting transverse movement of the bridge and everything it supports, as shown by the arrow L. The transverse carriage 394, in turn supports the X-ray tube head 112 by means of a telescoping tube assembly 154 which effectively functions as a vertically oriented linear bearing. The telescoping tube assembly 154 may be formed from a plurality of nested tubular structural members 156 having bearings to allow longitudinal slidable movement therebetween. Thus, the transverse carriage 394 and telescoping tube assembly 154 permit vertical movement of the X-ray tube head 112, as shown by the arrow C.

Movements along directions A and C are powered by a longitudinal drive 150 and a vertical drive 152 respectively. Drives 150, 152 are controlled by system controller 510 (FIGS. 1 and 2), and are preferably housed in the transverse carriage 394. Movements along directions A and C may also be performed manually by the operator. Transverse movement of the tube crane along direction L is not driven, and may only be accomplished manually by the operator.

The X-ray tube head 112 preferably comprises an X-ray tube head rotational drive (not shown), an X-ray tube assembly 158, an X-ray collimator 164, a control panel 160, and control handles 162 for use by the operator in selecting the position of the X-ray tube head 112. Information obtained from control panel 160 is preferably communicated to the system controller 510, which produces control signals to tube crane longitudinal and vertical drives to move the X-ray tube head 112 in the desired direction.

The X-ray tube head 112 is mounted on the telescoping tube assembly 154 for rotation about a transverse axis 188 as shown by the arrow B. Projection line 480 depicts the path of X-rays emitted by the X-ray tube head below collimator 164. Rotation of the X-ray tube head 112 allows the X-ray beam to be directed at various desired angles, such as toward the table 116 (which itself may rotate and translate) or the wall-mounted bucky 126. The X-ray tube head rotational drive (not shown) is controlled by system controller 510.

Thus, the tube crane 110, its associated drives 150 and 152, and the X-ray tube head rotational drive (not shown), cooperate to allow the system controller 510 to direct the X-ray tube head 112 to an arbitrary position on a reference plane parallel to the X-Z plane (within the range of travel provided by the mechanisms of the tube crane), and to point the emitted X-ray beam at an arbitrary angle along the reference plane. The transverse position of the reference plane is determined by the manually adjustable position of the tube crane transverse carriage 394, and normally is selected to be coincident with the longitudinal centerlines of table 116 and wall bucky 126. It is believed that providing three degrees of freedom for the position of the focal spot and the angular direction of the emitted X-ray beam, under control of the system controller 510, is sufficient for performing examinations using a variety of desirable radiographic, fluoroscopic, and tomographic imaging modes. However, a skilled artisan will appreciate that this embodiment may be easily modified to incorporate additional degrees of freedom if additional imaging modes are desired.

A tiltable patient support table 116 is provided to support a patient (not shown) during examination. The table 116 preferably also supports a digital imaging platform 114 for conducting examinations using fluoroscopic and stepped techniques. The table 116 preferably comprises a base 186 for supporting the table and for housing a table tilt drive (not shown). The table tilt drive simultaneously rotates the table about a transverse axis, as shown by arrow F, and translates the table. The translation is required to modify the effective center of rotation, thereby avoiding interference between the table and the floor. The base 184 preferably has a mounting and support plate 184 extending transversely to prevent the table from tipping due to the weight of the movable portion of the table, which is cantilevered from the base 184. Table 116 preferably further comprises a table top surface 176 movable in longitudinal and transverse directions as shown by arrows J and K by a 4-way drive system (not shown). The table top drive is controlled by the system controller 510. The movable table top 176 allows a patient to be moved to a desired position for examination.

Table 116 preferably further comprises an imaging media cassette or "bucky" 128 disposed in a horizontal shaft 178 below and parallel to the table top surface 176. The bucky has an interior region (not shown) for receiving an appropriate imaging medium, such as a piece of radiographic film (not shown). The bucky 128 also has a radiographic grid (not shown) for attenuating scattered radiation approaching the imaging medium. The bucky 128 is movable longitudinally within shaft 178 by a table bucky drive (not shown). Table bucky drive is controlled by the system controller 510. The table 116 may have a control panel 180 to allow the operator to select the position of the table top 176 and the bucky 180.

A digital imaging platform 114 is provided to perform fluoroscopy, digital image acquisition, and related imaging operations. The digital imaging platform comprises a support tower 174 extending vertically from the table, a support bracket 172 attached to the support tower 174, an X-ray tube assembly 182 disposed below the table top surface 176 and mechanically coupled to the support tower 174, a digital platform control panel 168 attached to the bracket 172, a positioning control handle 170, and an image intensifier and camera module 166 attached to the support bracket and disposed above the table top surface 176. The X-ray tube 182 and image intensifier module 166 are preferably fixedly mechanically coupled and aligned so that radiation from the X-ray tube 182 is directed toward a radiation receiving portion of the image intensifier module 166. The image intensifier module 166 is provided to convert received radiation to representative electrical signals 488 for viewing on a monitor 486 or for further processing by other components.

The digital imaging platform 114 is preferably mechanically coupled to the table 116 using suitable bearing means (not shown) permitting longitudinal translation of the platform 114 with respect to the table 116, as shown by arrow D. An imaging platform longitudinal drive (not shown) is controlled by the control system 510 to direct the imaging platform to a longitudinal position selected by the operator or, in some imaging modes, by the control system. The control handle 170 preferably includes sensors (not shown) for sensing the direction of force applied to the handle by an operator indicating a desired direction of movement of the platform 114. Information obtained from the sensors is preferably communicated to the system controller 510, which produces control signals to longitudinal drive to move the platform 114 in the desired direction.

The inventive imaging system 100 preferably further comprises a wall-mounted fixture 124 for supporting an additional imaging media cassette holder or bucky 126. The fixture 124 preferably comprises a vertical support member 190, and an imaging media cassette holder or "bucky" 126 mounted for vertical movement along the vertical support member 190, as shown by arrow H. The fixture 124 further comprises means 192 for sensing the vertical position of the bucky 126, and a cap member 194 disposed at the top of the vertical support 190 for securement to a support surface and for receiving electrical connections. The bucky 126 has an interior region (not shown) for receiving an appropriate imaging medium, such as a piece of radiographic film (not shown). The bucky 126 may have a radiographic grid (not shown) for attenuating scattered radiation approaching the imaging medium. The fixture 124 is preferably aligned with the reference plane containing the center line of the table 116. The fixture 124 may be secured to the floor 130 using a conventional mounting bracket 198 and suitable fasteners 202, such as bolts. The cap member 194 may be secured to the wall 132 using suitable conventional fasteners 196.

The position of bucky 126 may be manually controlled by the operator, but is not driven. However, the control system 510 receives an electrical signal 518 indicating the vertical position of the bucky 126 as sensed by sensor 192. A skilled artisan will appreciate that the preferred embodiment may be easily modified to drive wall mounted bucky 126 under control of control system 510 if necessary to accomplish a desired imaging mode.

A main control panel 120 interacts with control system 510 to allow the operator to select operating modes and other functional parameters of the inventive imaging system 100. A monitor 486, which may be any suitable television or computer display, receives electrical signals 488 from the image intensifier module 166 or other processing components and displays a corresponding image for use by the operator. An X-ray generator 118 provides electrical power for operating X-ray tubes 158 and 182. The X-ray generator converts 118 electrical power from a commercial AC power source to high-voltage DC at a selected voltage, for a selected duration, as instructed by control system 510. The X-ray generator also supplies power to heat the cathodes of the X-ray tubes 158, 182. The X-ray generator 118 preferably regulates the power supplied to the X-ray tube cathodes to achieve a desired tube operating current as instructed by the control system 510. A suitable X-ray generator 118 for use in this application is commercially available from Trex Medical Corporation, Continental X-Ray Division, 2000 S. 25th Avenue, Broadview, Ill. 60153 (the assignee of the present application), under the name TM Series Generator. Other commercially available X-ray generators could also be used, by modifying them for compatible communication with control system 510. Although the monitor 486, main control panel 120, and X-ray generator 118 are shown adjacent table 116, they may be remotely located to avoid exposure of the operator to X-rays.

As best seen in FIG. 1, the imaging system 100 incorporates an automatic brightness system (ABS) 204 and an automatic exposure control (AEC) 206, which are systems well known in the art for optimizing the quality of images produced in fluoroscopic and radiographic examinations. The ABS 204 is typically used during fluoroscopic examinations and may adjust various imaging system parameters in order to maintain the display of the image intensifier 166 at a consistent or selected average brightness. ABS systems which are known in the art may control such factors as X-ray tube high voltage, X-ray tube current, and the gain of the image intensifier 166. In the imaging system 100, the ABS 204 preferably primarily controls X-ray tube high-voltage to achieve the desired image intensifier brightness. The AEC 206 is typically used during radiographic exposures to terminate the exposure when a preselected integrated x-ray exposure (or dose) has been achieved. The AEC 206 may determine the exposure by measuring the X-ray dose rate delivered by the imaging system 100 using an ion chamber or the image intensifier screen brightness output, and then by integrating that value over time. The ABS 204 and AEC 206 are depicted in FIG. 1 as separate components coupled to the X-ray generator control 120 and control system 510. However, the functions of the ABS 204 and AEC 206 could also be integrated into the X-ray generator control 120 or another portion of the control system 510 so that separate components are not required.

According to one aspect of the present invention, means are provided for observing the patient optically in the area being examined, for detecting motion or other changes in the acquired optical image, and for controlling the imaging system responsively.

As best seen in FIG. 1, a video camera 408 may be provided for use in observing an area of the patient's body which is being examined by the imaging system 100. The camera 408 preferably provides a suitable output signal 412 which may be used for displaying the image on a monitor (such as monitor 486). The camera video output signal is preferably substantially conformant to a recognized official or industry standard for video signals so that the signal may be used by conventional display equipment, video signal processing equipment, and video-to-computer signal conversion equipment. However, cameras providing image information in other forms are available, and one of ordinary skill will appreciate that such cameras could be used in accord with the present invention by converting the signal to a standard format, or by modifying downstream equipment to accommodate the image information format provided by the camera.

Camera 408 is preferably affixed to the digital imaging platform 114 such that its field of view is always directed in the general vicinity of the examination region whenever the digital imaging platform is in use. However, other configurations may also be used. For example, although camera 408 is shown affixed to the digital imaging platform 114 in a position facing the patient, the camera could alternately be located elsewhere, and the optical image could be routed to it using a suitable arrangement of mirrors, prisms, or fiber-optic cables.

Camera 408 is used primarily for observing gross changes in its field of view. Therefore, any suitable small video camera may be used, including relatively inexpensive cameras designed for commercial, industrial, or surveillance applications. Because room lighting is often minimized during examinations, the camera 408 advantageously may be sensitive to both visible and infra-red light. A lens having a wide-angle of view is preferred to minimize the need to precisely aim the camera. A camera which uses a Charge-Coupled-Device image sensor may be preferred because several appropriate cameras of that type are readily commercially available.

The camera output signal 412 is preferably supplied to one or more motion detection means 406, 496 (FIGS. 2, 8; see also FIGS. 7 and 9). The camera 408, in cooperation with motion detection means 408, 496 and associated methods, allow the imaging system 100 to perform certain operations (or steps thereof) automatically, based on movement or changes observed in the image.

As discussed further in greater detail, image information from camera 408 (based on reflected visible or infra-red light) is one of three principal sources of information regarding motion (or other changes affecting the patient) which the inventive imaging system 100 may use in controlling its operation. The other two sources are: image information acquired by the digital imaging platform 114 during fluoroscopy (based on transmitted X-rays); and commands or requests for movement of the patient or the imaging system by the examiner. For convenience, we use the term "movement-related information" to refer to any information regarding motion (or other changes affecting the patient) originating from these sources. The imaging system 100 may use this movement-related information in a variety of ways to automate its operation, thereby improving examination quality and reducing the x-ray dose delivered to both the patient and the examiner. For example, during a pulsed fluoroscopy examination, the imaging system 100 may automatically adjust the pulse rate as appropriate when patient motion is detected. In other examination modes, the imaging system 100 may automatically switch from fluoroscopic mode to radiographic mode to make a radiographic exposure when motion is detected.

FIG. 2 is a general block diagram of a suitable control system 510 for use in coordinating the electrical and mechanical components of the inventive imaging system 100 to perform a variety of useful medical imaging examinations. Several different types of interconnections are provided between the components of control system 510 of FIG. 2. The legends "RS-232" and "RS-422" generally denote point-to-point serial data links which employ a standardized electrical line discipline. The legend "CAN Bus" denotes a serial data link among several interconnected components. The data is carried over a two-wire party line bus which may support a large plurality of independently addressed devices. Although four separate CAN bus links 516, 524, 526, and 540 are shown in the drawings, those links may be provided over as few as one, or as many as four, physical CAN busses, depending on traffic requirements. It is believed that satisfactory operation of the control system 510 may be obtained using two physical CAN busses. The electrical line discipline and message protocol of the CAN bus is described in the publication "CAN Bus Network" from Philips Semiconductor, Microcontroller Products Division. The legend "I/O Port" generally denotes non-serial signals which may be analog or digital.

As best seen in FIG. 2, the control system 510 comprises a universal control panel 160, a tomography control module 568, a radiographic/fluoroscopic control module 566, an X-ray generator control module 120, a digital platform control module 554, and a multi-axis motion controller 512.

The universal control panel 160 is located on the X-ray tube head 112, and allows the operator to select, inter alia, the system's examination mode, and certain operating parameters for radiographic and tomographic exposures. The universal control panel 160 communicates with the tomography control module 568 via a CAN bus link 526 and with the radiographic/fluoroscopic control module 566 via RS-232 link 530.

The tomography control module 568 operates when the imaging system 100 is performing a tomographic examination, and also operates any other time the overhead tube crane 110 is used. The tomography control module 568 issues requests to the radiographic/fluoroscopic control module 566 and the multi-axis motion controller 512 to drive the tube crane 110, X-ray tube head 112, and table bucky 128 in opposite directions about a fulcrum located on the desired tomographic imaging plane of the patient.

The digital platform control 554 communicates with digital platform 114, 556 and table 116, 556 via CAN bus 540, and with the digital platform display and control panel 168 via I/O ports 542. Those components, in turn, communicate with the table angulation drive 558 and the table-top surface four-way drive 560 via I/O ports 536 and 538. The radiographic/fluoroscopic control module 566 communicates with the universal control panel 160 via RS-232 link 530, the X-ray generator control 120 via RS-232 link 532, the digital platform control 554 via a CAN bus link 524, and the multi-axis controller 512 via can bus links 514 and 516. The X-ray generator communicates with the X-ray generator control using link means 534, which may be implemented using an RS-422 link and suitable I/O ports.

In addition, both the multi-axis motion controller 512 and the radiographic/fluoroscopic control module 566 communicate with the table angulation drive 558 via I/O ports 522, the table top four-way drive 560 via I/O ports 520, the wall bucky position sensor 586 via I/O ports 518, the table bucky drive 572, the X-ray tube angulation drive 576, and the tube crane drives 578 and 580 via a CAN bus link 516. In most imaging modes, the radiographic/fluoroscopic control module 566 transmits requests to the multi-access motion controller 512 to control in real time the movement of each driven component required to perform the examination. The multi-axis motion controller 512 is capable of simultaneous real-time control of motion along up to four axes. Although the multi-axis motion controller 512 can communicate with a large plurality of client devices, none of the examination modes in which the inventive imaging system 100 is intended to operate require simultaneous motion in more than four axes. However, the multi-axis motion controller 512 may be expanded to simultaneously control additional axes if new imaging modes so require.

The multi-axis motion controller 512 may be any appropriate real-time motion controller having sufficient throughput and compatible facilities for communicating with the drive systems and with the other control components of the control system 510. Any suitable commercially available motion controller capable of controlling simultaneously movements along at least four axes may be used. The tomography control module 568, the RF control module 566, the X-ray generator control 120, and the digital platform control 554 may be any implemented using any suitable control systems of sufficient computing and I/O capacity to control and interface with the required real-world devices. For example, each of these controllers may be constructed using conventional microprocessor and interface technology as is known in the art. Off the shelf general-purpose microcomputer-based control products may be used to implement these controllers, or each controller may be constructed by selecting only those facilities required to achieve the respective control functions.

According to an aspect of the present invention, means are provided for analyzing one or more video (or similar) signals representing optical or X-ray images acquired from the patient and detecting motion or change in the image over time.

As best seen in FIG. 2, one or more motion detection means 406, 496 may be provided to analyze video signals (or other similar signals) generated by the video camera 408 and/or the image intensifier 166 to determine whether motion, or another change of interest, is occurring in an observed image. As discussed previously, the imaging system 100 may receive information from three principal sources indicating that motion (or another relevant change in an observed image), is occurring, and may use that information to automatically control its operation. For convenience, we use the term "movement-related information" to refer to any such information originating from these sources. A first source of such movement-related information is a video signal 412 representing an ordinary optical image (i.e., an image resulting from reflected visible or infra-red light) produced by camera 408 which is trained on the portion of the patient being examined. An advantage of using an ordinary optical image of the patient to detect movement is that the image information may be acquired without exposing the patient to examiner to x-rays.

A second source of such movement-related information is a video (or similar) signal 414 representing the image acquired by the image intensifier component 166 of the digital imaging platform 114. The image information from this source results from transmission of x-rays through a portion of the patient undergoing examination. Thus, to acquire image information from the image intensifier 166, the patient must be exposed to x-rays.

A third source of movement-related information is produced from operator-actuated movement controls. Most of the movable components of the imaging system, including the patient support table 116, are driven under the control of the control system 510 at the request of an operator. Accordingly, whenever the operator requests movement of the patient or the imaging system, the control system 510 is aware of such movement and can respond accordingly. An advantage of using information regarding movements requested through operator-actuated control is that it may be acquired without exposing the patient to X-rays. Another advantage of using this source is that it is predictive—i.e., information about pending movements is acquired before the movement occurs.

As best seen in FIG. 2, image information signals 412 and 414 produced by camera 408 and image intensifier 166 respectively may be provided to either or both of first and second motion detection means 406, 496. Since information from the operator-actuated movement controls is acquired directly, it need not be processed by the motion detection means. First and second motion detection means provide similar motion detection functions, but are implemented differently, and may be considered alternatives. Each of the motion detection means 406, 496 are shown with two functional motion detector units or channels, and the both the image information signal 412 (from camera 408) and image information signal 414 (from image intensifier 166) are shown routed to both motion detector means 406, 496. However, in a commercial embodiment of the invention, only one of the motion detection means 406, 496 would be implemented, and each of the image information signals would be routed to a respective unit or channel of the motion detection means which was implemented. Each of the motion detection means 406, 496 (or each independent channel thereof) provides a motion detect output signal on lead or communications path 482 to the digital platform control 554, and may exchange other communications with the digital platform control 554 over that path.

Preferably, a motion detection user interface 458 (FIGS. 2, 8) is provided to allow an operator of the imaging system 100 to select a motion detection threshold and to define regions or "windows" of interest for motion detection (e.g. windows 820 and 830; FIG. 5). The motion detection threshold control allows the user to define the amount of change in an image, over time, which is needed in order to determine that motion has occurred. The internal operation of the motion detection means 406, 496 is discussed further in detail (see FIGS. 7–9), but in summary, the motion detection means measure the amount of change in the image over time; if the amount of change exceeds the user-defined threshold, the motion detection means 406, 496 determines that motion has occurred, and provides that information to the digital platform control using the motion detection output signal 474. The window controls allow the user to define particular regions or "windows" 820, 830 (FIG. 5) of the image to be of interest in motion detection. For example, as discussed further in detail, the motion detection means 406, 496 may be instructed to respond to movement or change throughout the entire image, or to movement or change within a single window thereof, or to movement or change sequentially affecting two independent windows thereof.

Each of the motion detection means 406, 496 (or each independent channel thereof) preferably provides a video output signal 488 which may be similar to the input signal provided to that motion detection means 406, 496. The output signal 488 may be supplied to a monitor 486 so that it may be displayed to the user. The video output signal 488 is preferably keyed or otherwise modified by the motion detection means to indicate the user-selected boundaries 812, 814, 816, 818, 822, 824, 826, 828 (FIG. 5) of the motion detection windows 820, 830 (FIG. 5) in the displayed image 810 (FIG. 5). Techniques for indicating the boundaries are known in the art.

Although the motion detection user interface 458 is depicted as a control panel with discrete controls, the user interface 458 could be implemented using any appropriate control means. For example, the user interface 458 could also be implemented as functions of one or more of the general purpose control panels used to control the imaging system 100, such as the main (X-ray generator) control panel 120 (FIGS. 1–2), or the digital platform control panel 168 (FIGS. 1–2). In addition, the user interface 458 may be implemented using any suitable input and output devices, including, for example, analog controls and displays, rotary encoders, conventional computer keyboards and displays, and uncommitted, general purpose, or software-defined controls on a computer based control panel. The motion detection user interface 458 may communicate with each of the motion detection means 406, 496 (or each independent channel thereof) using a signal lead (or communications path) 474.

First motion detection means 406 may be implemented using one or more stand-alone motion detection modules or circuits for applications of the imaging system 100 in which an accompanying image processing system is not provided. FIG. 8, discussed further in detail, is a block diagram of a single-channel stand-alone motion detection module or circuit 410 constructed according to the present invention. The stand-alone motion detection module 410 of FIG. 8 may be implemented using any suitable digital and analog circuitry.

As best seen in FIG. 2, the first motion detection means 406 provides two independent motion detection channels 410a and 410b, each implemented using the circuit 410 of FIG. 8, and each capable of detecting motion or relevant changes in a single video signal or stream of video information). However, any desired number of motion detection channels may be provided by replicating the circuit 410. FIG. 9, discussed further in greater detail, is a flow diagram illustrating a method according to the present invention of detecting motion in a video image using a stand-alone motion detection module or circuit 410 of the type shown in FIG. 8.

In some applications, the imaging system 100 is equipped with an image processing system which allows the user to manipulate the images produced by the system in various ways, such as by improving image contrast or applying filters or other image operators. Such image processing systems often have high-performance general-purpose or special purpose processing units which are capable of performing the required motion detection function in real-time. Accordingly, second motion detection means 496 may be implemented using a suitable image processing system, in conjunction with appropriate motion detection software or firmware. Several image processing systems are commercially available which may be used for motion detection, in addition to the image processing tasks for which image processors are normally applied in radiology applications. For example, image processors suitable for use in implementing the second motion detection means 496 are commercially available from INFIMED Inc., 121 Metropolitan Drive, Liverpool, N.Y. 13088, under the designations "FC 2000" and "QL 2000;" and from CAMTRONICS Ltd., 900 Walnut Ridge Drive, Heartland, Wis. 53029, under the designation "VIDEO PLUS." FIG. 7, discussed further in greater detail, is a flow diagram illustrating a method 922 according to the present invention of detecting motion in a video image using a typical commercially-available image processing system.

As best seen in FIG. 2, the second motion detection means 496 comprises two image processing "channels" 490a and 490b. The two channels may, but need not, correspond to separate physical components. Depending on the capabilities of the image processor used to implement the motion detection system 496, a single image processor module (or processing unit) may be capable of performing the motion detection function for multiple video signals; alternatively, a separate processor module or channel may be required for each video signal to be processed. Although the second motion detection means 496 is shown having two channels for motion detection, any reasonable number of motion detection channels could be provided by selecting higher performance image processors, or by obtaining additional processors.

Although the internal organization of commercially available image processors may vary, the image processing functions are generally performed using digital processing techniques. Each of the image processing channels 490a, 490b is shown with an interface 492a, 492b for converting video signals 412, 414 received from the camera 408 and image intensifier 166, respectively, in analog form, into a digital form for such processing. However, if one or both of the video signals 412, 414 are supplied in digital form, then the corresponding interfaces 492a, 492b may be omitted. The motion detection blocks 494a, 494b shown as part of the image processing channels 490a, 490b correspond to those portions of the channels which provide the motion detection functions; the motion detection blocks 494a, 494b may, but need not, correspond to separate physical components.

According to an aspect of the present invention, means are provided for achieving a rapid transition between radiographic and fluoroscopic imaging modes of the imaging system 100. Radiographic exposures are typically performed at relatively high X-ray tube currents (approximately 100–1000 mA) over a brief interval. Fluoroscopic examinations are typically performed at low average X-ray tube current (approximately 0.5 to 3 mA) over long intervals. For a particular X-ray tube, at a selected X-ray tube voltage, the X-ray tube current is primarily determined by the X-ray tube cathode (filament) temperature, which, in turn is controlled by the current flowing through the filament. When it is desired to operate the X-ray tube at a different current, it takes time for the cathode to heat or cool to the required temperature. In prior art imaging systems, a substantial delay (of approximately one second) has been imposed during the transition between fluoroscopic and radiographic imaging modes to allow the cathode to reach the desired temperature. As a result, prior art imaging systems may miss some rapidly-occurring events.

In contrast, while the inventive imaging system 100 is performing a fluoroscopic examination, the system can initiate a radiographic exposure essentially immediately upon request therefor. When the request is received, the imaging system 100 uses information which was acquired by the automatic brightness system (ABS) regarding the fluoroscopic image brightness during the immediately preceding fluoroscopic examination to determine the appropriate technique (X-ray tube voltage and current) for the radiographic exposure. The imaging system 100 begins the radiographic exposure immediately, setting the X-ray tube voltage to be used for the radiographic exposure to the voltage previously determined by the ABS during fluoroscopy, and setting the filament current to that needed to ultimately produce the required X-ray tube current. Because the X-ray tube cathode is initially at the temperature used for fluoroscopy, x-ray tube current is also initially at the relatively low value used for fluoroscopy but increases the cathode is heated. The exposure is terminated automatically when a desired exposure level, as determined by the mA•S control (when the operator has selected the "normal" mode), or the AEC 206 (when operator has selected the AEC mode), has been reached. As a result of beginning the radiographic exposure immediately, the imaging system 100 can acquire at least some image information during a rapidly occurring event, instead of entirely missing the event as might occur when using prior art imaging systems.

Similarly, if it is desired that the imaging system 100 return to the fluoroscopic examination mode after performing a radiographic exposure, the inventive imaging system 100 can do so immediately, in contrast to prior art systems which have imposed a delay. When the radiographic exposure is completed, the x-ray tube cathode is relatively hot. If the X-ray tube voltage were maintained at the same value used in the radiographic exposure, the high cathode temperature would result in unacceptably high x-ray tube current (and X-ray output) for fluoroscopic examination. Therefore, using the fluoroscopic technique information determined in the previous fluoroscopic exposure, the imaging system 100 determines the correct (lower) X-ray tube voltage required in order to achieve an equivalent X-ray output at the high cathode temperature. At the end of the fluoroscopic exposure, the imaging system 100 immediately reduces the filament current to initiate cooling of the cathode, lowers the x-Ray tube voltage, enters the fluoroscopic mode, and enables the automatic brightness system (ABS) 204. As the filament cools, reducing the x-ray tube current, the ABS 204 automatically adjusts the x-ray tube voltage to maintain a consistent brightness on the image intensifier screen.

FIGS. 3a–3c are a flow diagram illustrating an exemplary method 610 according to the present invention for controlling the imaging system 100 in order to provide, when appropriate, rapid transitions between radiographic and fluoroscopic imaging modes. The functions required to implement the method 610 are generally provided by the x-ray generator 118 (FIG. 1) and the control system 510 (FIG. 2), including the x-ray generator control 120 (FIGS. 1–2), the ABS 204 (FIG. 1) and the AEC 206 (FIG. 2).

The method 610 is invoked at step 612 when the operator selects the "FLUORO-RAD-FLUORO" fast transition option by means of a set-up mode of the imaging system 100. Selecting this option enables the imaging system 100 to rapidly perform radiographic exposures while in the midst of a fluoroscopic examination. Step 614 is the beginning of a primary loop in which the system determines, at any particular moment, whether to enter the radiographic exposure mode, enter the fluoroscopic examination mode, or to await further requests, and whether to attempt a rapid or standard transition between modes. In step 614, the system determines whether a radiographic exposure is requested. If a radiographic exposure has not been requested, the method jumps to step 634, to continue its determination of the requested exposure mode. However, if a radiographic exposure has been requested, the method continues in step 616, in which the system determines whether a fluoroscopic examination is in progress. If a fluoroscopic examination is not in progress, the method jumps to step 622 to begin a sequence of steps for performing a standard radiographic exposure. If a fluoroscopic examination is in progress, the method continues in step 618, where the system determines whether a two-factor exposure mode has been selected. In the two-factor exposure mode, the operator sets the x-ray tube voltage and mA•S parameters, and the imaging system terminates the exposure when the desired mA•S has been reached. If the AEC option is selected, the exposure is similarly terminated when the desired or dose has been reached.

If a two-factor exposure mode has not been selected (which means that the operator has specified a particular X-ray tube current), the imaging system 100 cannot perform a rapid transition because the rapid transition requires varying the X-ray tube current, which then will not correspond to the current selected by the operator. Accordingly, the method jumps to step 622 to begin the standard radiographic exposure sequence. If a two-factor exposure mode has been selected, then the method continues in step 620, the beginning of the a sequence of steps resulting in a rapid FLUORO-to-RAD transition. Thus, the requirements for performing a FLUORO-to-RAD transition. Thus, in order to perform a rapid FLUORO-to-RAD transition, a radiographic exposure must be requested, the system must already be performing a fluoroscopic exposure, and a two-factor exposure mode must have been selected.

In step 620, the system selects the x-ray tube voltage for use in the radiographic exposure to be the same as that determined by the ABS 204 during the immediately previous fluoroscopic examination. At step 626, the system determines the required ultimate x-ray tube current using technique information determined by the ABS 204 during the immediately previous fluoroscopic examination. In some applications, an X-ray tube having 2 or more filaments, each of a different size and having a different maximum emission current rating, may be employed. The smaller filament provides higher resolution, and is therefore preferred when it can be used. If the required X-ray tube current exceeds the emission capability of the smaller filament, the system selects the larger filament.

At step 628, the system begins the radiographic exposure immediately, while the filament is heating and the x-ray tube current is rising. In step 630, the imaging system 100 terminates the radiographic exposure when it determines that the preselected value of mA•S has been reached. If the AEC 206 has been enabled, then the imaging system 100 terminates the radiographic exposure when it determines that the preselected dose has been delivered, or the preselected value of mA•S has been reached. If the AEC 206 has been enabled, the mA•S control serves as a backup to preclude delivery of an excessive x-ray dose.

Step 632 represents the end of this sequence, in which a radiographic exposure is performed in conjunction with a rapid transition from fluorographic mode to radiographic mode. In step 634, the imaging system determines whether the operator has requested that the system return to the fluoroscopic examination mode once the radiographic exposure is completed. If the "FLUORO" mode was not requested, the method loops back to step 614, whereupon the primary mode-determination loop is restarted.

However, if in step 634, the "FLUORO" mode was selected, the method continues with step 636, in which the system selects small focal spot of the X-ray tube for use. The small focal spot is preferred whenever the x-ray tube current is low enough to permit its use because it provides higher resolution. The focal spot is the projection of the filament on the image plane. Hence, selecting the small focal spot is equivalent to selecting the small filament.

In step 644, the system determines whether the ABS 204 is enabled. If the ABS 204 is enabled, then the method continues with step 646, which is the first in a sequence of steps for performing a fast transition from radiographic to fluoroscopic mode. At the termination of the radiographic exposure, the x-ray tube cathode is at the high temperature required to supply the relatively-high x-ray tube current required for radiography, and it cannot be instantaneously cooled.

For a particular combination of X-ray tube, and filament the x-ray tube radiation output is directly proportional to the x-ray tube current, and approximately proportional to the fifth power of the x-ray tube high voltage. When the imaging system returns to fluoroscopic mode, it is desirable to provide the same image-intensifier brightness as was previously used during fluoroscopy, and therefore, it is desirable to provide the same fluoroscopic mode x-ray tube output as was previously used. Although the x-ray tube current cannot be instantaneously controlled, the X-ray tube voltage can be (within a few milliseconds). Therefore, when a fast transition from radiographic to fluoroscopic mode is to be performed, the imaging system determines an initial X-ray tube voltage which is required, when the tube is operated at the initially higher current, to cause the tube to produce the desired fluoroscopic mode x-ray output. This initial voltage is always lower than the voltage used during the radiographic exposure.

As the x-ray tube filament cools, the x-ray tube current drops, and the x-ray tube voltage must be correspondingly increased to maintain a consistent x-ray output and image intensifier brightness. This function is automatically performed by the ABS 204. Thus, if the ABS 204 is not enabled, the desired x-ray output cannot be maintained, and the imaging system 100 cannot perform a rapid transition. In that case, the method continues with step 660, which is the first in a sequence of steps for performing a normal transition from radiographic to fluoroscopic mode.

If ABS is enabled, the rapid RAD-to-FLUORO transition sequence beginning with step 646 is performed. In step 646, the imaging system 100 determines the initial x-ray tube voltage required to cause the tube to produce the desired fluoroscopic mode x-ray output when operated at the initially high current (resulting from the filament being at the high temperature required for the radiographic exposure). The desired output is typically the same as was used during fluoroscopy immediately prior to the radiographic exposure, so that the image intensifier brightness will be the same. The initial x-ray tube voltage will be lower than the voltage used during the just-completed radiographic exposure.

In step 648, the fluoroscopic examination is started immediately, using the initially high x-ray tube current, and the initially lowered x-ray tube voltage. The filament current is reduced to allow the cathode to cool, which, in turn, causes a reduction in the x-ray tube current. In addition, when the X-ray tube is operating (i.e., high voltage is applied), the filament cools much faster than when the X-ray tube is in an idle condition. Thus, the rapid RAD-to-FLUORO transition of the present invention causes the X-ray tube current to return to a value appropriate for fluoroscopy more rapidly than would otherwise be accomplished. In step 650, as the filament cools, the x-ray tube current falls, the ABS correspondingly increases the x-ray tube voltage to maintain constant image intensifier brightness (and, effectively, constant x-ray tube output). Eventually, the x-ray tube current falls, and the x-ray tube voltage rises, to their normal fluoroscopic levels.

Step 652 represents the end of this sequence, in which a rapid transition from radiographic mode to fluoroscopic mode has been performed. In step 654, the fluoroscopic examination continues under the supervision of the ABS 204, which maintains a constant brightness on the display of the image intensifier 166. In step 656, the imaging system determines whether the fluoroscopic examination is still in progress, or has been terminated by the operator. If the examination has been terminated, the method loops back to step 614, whereupon the primary mode-determination loop is restarted. Otherwise, the method returns to step 654, and the loop consisting of steps 654 and 656 are performed until the examination is terminated.

If, in step 644, the imaging system determined that the ABS 204 was not enabled, the method continues at with step 660, which is the first in a sequence of steps for performing a normal transition from radiographic to fluoroscopic mode. In step 660, the imaging system sets the x-ray tube voltage and current to operator-selected values. The x-ray tube current is primarily determined by the cathode temperature, which, in turn, is controlled by the filament current. Accordingly, the system sets the filament current to that required to produce the desired x-ray tube current, but it takes some time for the cathode to cool to the desired temperature. In step 662, the imaging system 100 determines whether the cathode has cooled to the desired temperature. If the cathode is still too hot, step 670 is performed, in which the system delays for a predetermined interval to allow the cathode to cool, and then the method loops back to step 662. The loop consisting of steps 670 and 662 is performed until the filament reaches the desired temperature. Once the filament is ready for use, step 664 is performed, in which the fluoroscopic examination is initiated using the operator-selected technique.

Step 666 represents the end of this sequence, in which a normal transition from radiographic mode to fluoroscopic mode has been performed. In step 668, the imaging system determines whether the fluoroscopic examination is still in progress, or has been terminated by the operator. If the examination has been terminated, the method loops back to step 614, whereupon the primary mode-determination loop is restarted. Otherwise, the method returns to step 668, and the fluoroscopic examination continues until terminated by the operator.

If, in steps 614–618, the system determined that a radiographic exposure was requested, but a rapid transition to radiographic mode could not be performed, the method jumps to step 622 to begin a sequence of steps for performing a standard radiographic exposure. In step 622, the imaging system 100 sets the x-ray tube voltage to a value selected by the operator. In step 624, if the x-ray tube includes multiple filaments, the imaging system selects the filament appropriate for the operator-selected x-ray tube current. In step 638, the system sets the x-ray tube current to a value selected by the operator. In step 640, the system supplies filament current to the x-ray tube and waits until the filament reaches the proper temperature to produce the operator-selected x-ray tube current. Then the system performs a normal radiographic exposure using the operator-selected technique.

Step 642 represents the end of this sequence, in which a radiographic exposure is performed in conjunction with a normal transition radiographic mode. The method loops back to step 614, whereupon the primary mode-determination loop is restarted.

As disclosed above in connection with FIGS. 1–2, the imaging system 100 may receive information from several sources indicating that motion (or another relevant change detected in an optical or x-ray image acquired from the patient), is occurring, and may use that information to automatically control its operation. According to an aspect of the present invention, the imaging system 100 may use movement-related information to advantageously reduce the x-ray dose received by the patient and the examiner during a pulsed fluoroscopy examination, while continuing to provide high-quality images, even when motion is occurring.

The term "pulse" refers to a short burst of x-rays emitted at regular intervals to enable a fluoroscopic image to be acquired. Pulsed fluoroscopy may be preferred over continuous fluoroscopy in some applications because the individual x-ray pulses may be emitted at a higher instantaneous dose rate while still maintaining a very low average dose rate. Images acquired at higher instantaneous dose rates generally exhibit improved signal-to-noise ratio.

Although pulsed fluoroscopy systems providing several user-selectable pulse rates are known, examiners do not always select the optimum pulse repetition rate during all phases of an examination. It is generally desirable to use a higher pulse repetition rate whenever relative motion between the patient and the imaging system occurs (or is expected to occur), or whenever an event causing a change in the image occurs or is expected. A higher pulse rate eliminates or reduces the "jerky" appearance of motion. However, when no motion or change in the image is expected, a lower pulse repetition rate is strongly preferred because it results in a substantially lower dose to both the patient the examiner. Despite the availability in prior art imaging systems of a range of selectable pulse repetition rates, it has been observed that examiners often will operate the systems at one of the higher rates throughout the fluoroscopy examination, even during periods when no movement or change in the image is expected.

FIGS. 4a–4b are a flow diagram illustrating an exemplary method 710 according to the present invention for controlling the imaging system 100 in response to movement-related information in order to responsively select the fluoroscopic pulse rate and other imaging system parameters.

The functions required to implement the method 710 are generally provided by the control system 510 (FIG. 2), x-ray generator 118 (FIG. 1) and the x-ray generator control 120 (FIGS. 1–2).

The method 710 begins in step 712. In step 714, the control system 510 prepares to use an initial fluoroscopic pulse rate during portions of the examination in which no movement or other significant change is expected in the acquired fluoroscopic image. Preferably, the imaging system 100 is capable of providing a plurality of pulse rates appropriate for fluoroscopic examinations ranging from high pulse rates suitable for smoothly reproducing motion, to low rates suitable for observing an essentially static image. For example, the imaging system may provide selectable pulse rates of approximately 30, 15, 7.5, 3.8, and 1.9 pulses per second (PPS). The 30 PPS rate is approximately equal to the frame repetition rate used in television systems and is considered suitable for observing full-speed motion. Other rates may also be provided. As is known in the art, the imaging system fluoroscopic display preferably comprises suitable image memory (not shown) so that the most recently acquired image is continuously displayed between pulses. The "initial" pulse rate established in step 714 is preferably selected by the user from the lower end of the range of available rates, to minimize the dose to which the patient and examiner are exposed when no movement is expected.

In step 716, the control system 510 prepares to use an initial frame integration rate during portions of the examination in which no movement or other significant change is expected in the acquired fluoroscopic image. The step is optional and may be omitted if the frame integration means is not available or if the examiner elects not to use it. Frame integration is a known method of reducing noise and minimizing artifacts in essentially static images by accumulating and displaying image information from multiple views or "frames" of the same image acquired over time. Each time a fluoroscopic pulse is emitted, the resultant acquired image is stored as a frame of image information. By effectively averaging the value of each pixel over multiple acquisitions, frame integration reduces the effect of transient changes in the image, such as image noise. The frame integration rate refers to the number of previous frames of image information used in displaying the present information. Preferably, a plurality of selectable rates may be provided. In a commercial embodiment of the imaging system 100, for example, rates of 1, 2, 4, 8, and 16 may be selected. Higher rates improve noise reduction in static images, but increase artifacts in moving images, because image features are shown at multiple (old) locations. The "initial" frame integration rate established in step 716 is preferably selected by the user from the higher end of the range of available rates, to maximize noise reduction when no movement is expected.

In step 718, the control prepares to use an initial edge enhancement level during portions of the examination in which no movement or other significant change is expected in the acquired fluoroscopic image. The step is optional and may be omitted if the edge enhancement means is not available or if the examiner elects not to use it. Edge enhancement is a known method of improving the visibility of image features which may represent the edges of structures. Higher edge enhancement levels may be preferred for observing moving images. When observing static images, less or no edge enhancement may be needed. The "initial" edge enhancement level established in step 718 is preferably selected by the user from the lower end of the available rates.

Step 720 is the first step of a primary loop in which the control system 510 waits for a fluoroscopic examination to start, waits for an indication of movement or a significant change in an image acquired from the patient, and if such indication is received, responsively adjusts the parameters of the fluoroscopic examination to those suitable for observing the moving or changing fluoroscopic image.

In step 720, the control system 510 determines whether the fluoroscopic examination is in progress. If the fluoroscopic examination is not in progress, then the control system 510 need not alter examination parameters in response to motion, and the method loops back to step 720 until the examination begins. Also in step 720, whenever a fluoroscopic examination begins, the control system 510 causes operation at a high fluoroscopic pulse rate for a brief interval in order to stabilize the operation of the image intensifier 166 and the automatic brightness system (ABS) 204. For example, the system may operate at the 30 PPS rate for a stabilization period 8 pulses, in order to rapidly stabilize the image intensifier 166 and the ABS 204. Once the stabilization period is complete, the fluoroscopic pulse rate is maintained at the slower initial rate.

In step 722, the control system 510 determines whether the operator has requested movement of the digital imaging platform 114 (also referred to as the "fluoro carriage"). In step 724, the control system 510 determines whether the operator has requested movement of the patient support table 116. The imaging system 100 provides driven motion of the digital imaging platform 114 and the patient support table 116 in response to operator requests therefor. The operator communicates these requests using motion control switches and handles located on the digital imaging platform control panel 168, digital imaging platform positioning control handle 170, and patient support table control panel 180. The control switches are operatively connected to the control system 510. Thus, whenever the operator requests movement of the digital imaging platform 114 or the table 116, the control system 510 is aware of the request. If, in steps 722 or 724, a movement request was detected, the method jumps to step 730. If no movement was detected, the method continues at step 726.

In step 726, the control system determines whether motion, or another relevant change, has been detected in the fluoroscopic image being acquired in the examination, or the optical image of the examination region. Either or both of the video images from the image intensifier 166 and the optical camera 408 may be analyzed by motion detection means 406, 496 (FIG. 2; see also FIGS. 7–9). If motion or other image changes was detected, the method jumps to step 730. If no motion was detected, the method continues with step 728. In step 728, if the examination parameters were changed, the control system resets these parameters to their initial values. The imaging system continues the fluoroscopic examination using the initial parameters. Then method returns to step 720 to re-execute the primary loop.

In steps 730–736, the control system modifies the fluoroscopic examination parameters in response to the motion determined in steps 722–726. In step 730, the control system 510 determines the rate of motion which was requested or detected. For imaging system movement requested by the operator, the control system 510 has definitive information as to the rate of that motion. For motion detected in a video signal, the motion detection means may determine the rate at which the leading edge of a moving feature advances on a pixel-by-pixel basis using well-known methods.

In step 732, the control system proportionally increases the fluoroscopic pulse rate to a rate appropriate for observing the fluoroscopic image in which motion is occurring at the determined rate. Preferably, the control system 510 selects a faster fluoroscopic pulse rate when the determined rate of motion is greater, in order to provide improved image quality.

In step 734, the control system proportionally reduces the frame integration rate (if frame integration is enabled) to a rate appropriate for observing the fluoroscopic image in which motion is occurring at the determined rate. Preferably, the control system 510 selects a lower frame integration rate when the determined rate of motion is greater, in order to provide improved image quality.

In step 736, the control system proportionally increases the edge enhancement level (if edge enhancement is enabled) to a level appropriate for observing the fluoroscopic image in which motion is occurring at the determined rate. Preferably, the control system 510 selects a higher edge enhancement level when the determined rate of motion is greater, in order to provide improved image quality.

In some applications, it may not be desirable or necessary to modify the fluoroscopic pulse rate, frame integration rate, and edge enhancement level proportionally. In such applications, step 730 may be omitted, and steps 732, 734, and 736 may modify the fluoroscopic pulse rate, frame integration rate, and edge enhancement level, to respective user-selected values for use when motion is present. Step 730, and the "proportional" features of 732, 734, and 736 are shown in broken lines to indicate that proportional adjustment of these parameters is optional.

In steps 738–742, the control system 510 determines whether to return to step 728 to reset the fluoroscopic examination parameters to their initial values. In step 738, the control system 510 determines whether the fluoroscopic examination is still in progress. If the examination is not still in progress (i.e., if the operator has terminated the examination), the method jumps to step 728. Otherwise, in step 740, the control system 510 determines whether motion of the digital imaging platform 114 was the reason for using the motion-specific parameters, and if so, whether the motion has been de-selected. If both of those conditions are true, then is it no longer necessary to use the motion-specific fluoroscopic examination parameters, and therefore, the method jumps to step 728 to reset them to their initial values. Otherwise, the method continues at step 742.

In step 742, the control system 510 determines whether motion of the patient support table 116 motion of the patient support table 116 was the reason for using the motion-specific parameters, and if so, whether the motion has been de-selected. If both conditions are true, then is it no longer necessary to use the motion-specific fluoroscopic examination parameters, and therefore, the method jumps to step 728 to reset them to their initial values. Otherwise, the method loops back to step 738 to continue the fluoroscopic examination using the motion-specific parameters.

Whenever the method reaches step 728, the control system resets the fluoroscopic examination parameters to their initial values, and returns to the beginning step 720 of the primary loop. If the examination is still in progress, then the control system executes the loop repeatedly until motion is again detected. If the examination is not still in progress, then the control system waits at step 720 until an examination begins.

The method 710 allows the imaging system 100 to perform fluoroscopic examinations at low fluoroscopic pulse rates except when motion is detected or requested, at which time the imaging system automatically uses a higher pulse rate. This advantageously reduces the dose delivered to the patient and examiner, while providing high image quality when motion or image change occurs. It also minimizes inconvenience to the examiner by eliminating the need to manually change the pulse rates as the examination progresses from phase to phase, and eliminates the incentive to the examiner to operate the system at a high pulse rate throughout the examination. Although the method describes changing several specific fluoroscopic imaging parameters in response to requested (forecast) or detected motion, any other parameters controlled by control system 510 could also be responsively controlled.

Automatic control of certain imaging system functions based on detected or forecast patient motion can provide improved examination results because the time required to electronically detect the movement and initiate the desired function can be much smaller than that required when observation by a human operator is involved. Further, although the attention of a human operator stray, the automatic system remains constantly vigilant, and therefore less likely to miss an movement of interest.

In addition to improving examination quality, the automatic motion detection may result in the delivery of a reduced total X-ray dose to both the patient and the examiner. If an event of interest is missed, either the patient must be re-examined, or the patient must be instructed to perform the movement or event again. In either case, missing the event results in an increased dose. By avoiding missed events, the automatic motion detection of the present invention can result in a lower x-ray dose.

According to a further aspect of the present invention, the imaging system 100 may use the movement-related information to control the progress of a preprogrammed radiographic/fluoroscopic examination in which coordinated movement of the patient and/or the imaging system is carried out simultaneous with or interspersed among radiographic and/or fluoroscopic exposures.

FIG. 5 is a diagram showing schematically an exemplary image display 810 produced by the imaging system 100 in an examination in which the progress of a radio-opaque die or contrast medium 832 progresses through a portion of a patient's body subject to examination. This procedure is used in various imaging system applications. For example, in peripheral angiography examinations, the contrast medium is injected into the patient's blood stream. The progress of the contrast medium is observed fluoroscopically as it moves through the patient's circulatory system. The contrast medium enhances the radiographic appearance of the circulatory vessels. In order to create a radiographic record of the structure of the patient's circulatory system, it is desired to make a complete series of radiographic exposures as the contrast medium progresses through various locations.

To minimize the dose to which the patient is exposed, it is preferred that the exposure locations be selected such that the exposures produce complete, but minimally overlapping coverage. In order to accomplish this, the imaging system components must be precisely moved to the desired locations, and the exposures must be initiated, in coordination with the movement of the contrast medium. In prior art systems, this coordination was performed by predicting the rate of contrast medium progression and scheduling the exposures at particular times, or by having an examiner observe the progression of the contrast medium in the fluoroscopic image and command the radiographic exposure when the contrast medium is observed to have reached the desired location. In the past, such coordination has often proved imperfect, with the results that: examination quality has been degraded; excessive overlapping exposures, or complete reexaminations have been required; and the dose to the patient has been higher than desired.

FIGS. 6a–6c comprise a flow chart illustrating an exemplary method 840 of controlling the imaging system 100 automatically performing a predefined sequence of radiographic and fluoroscopic examinations steps in coordination with the observed movement of contrast medium through a patient. The method 840 will be discussed in connection with FIG. 5.

The method 840 begins in step 842. In step 846, the control system 510 prepares to use an initial fluoroscopic pulse rate during portions of the examination in which no movement or other significant change is expected in the acquired fluoroscopic image. The "initial" pulse rate established in step 846 is preferably selected by the user from the lower end of the range of available rates. As shown in result block 844, this minimizes the dose to which the patient and examiner are exposed.

In step 850, the control system 510 prepares to use an initial frame integration rate during portions of the examination in which no movement or other significant change is expected in the acquired fluoroscopic image. The step is optional and may be omitted if the frame integration means is not available or if the examiner elects not to use it. The "initial" frame integration rate established in step 850 is preferably selected by the user from the higher end of the range of available rates, to maximize noise reduction when no movement is expected.

In step 852, the control system 510 prepares to use an initial edge enhancement level during portions of the examination in which no movement or other significant change is expected in the acquired fluoroscopic image. The step is optional and may be omitted if the edge enhancement means is not available or if the examiner elects not to use it. The "initial" edge enhancement level established in step 852 is preferably selected by the user from the lower end of the available rates. Block 848 indicates that the result of steps 850, 852 is improved image quality.

In step 854, the user selects the "auto center" option, which enables an examination mode in which the imaging system 100 performs a series of radiographic exposures at pre-planned locations with respect to the patient. The imaging system 100 and its control system 510 manages movement of the digital imaging platform 114 and the patient support table 116, and coordinates radiographic and fluoroscopic exposures according to instructions programmed by the operator in step 854.

In step 856, the user employs the motion detection user interface 458 (FIGS. 2, 8) to select the size and positions of the windows of interest 820, 830 (FIG. 5). Windows 820, 830 define the portions of the fluoroscopic image 810 which will be analyzed for movement or other significant change by the motion detection means 806, 896. The user may elect to use one, two, or more windows. For example, the operator may elect to use one window per leg, in an examination of both legs, for a total of four windows. When operating in the one-window mode, the imaging system 100 moves to a user-programmed location, and awaits a movement indication. As the contrast agent progresses through location 832a to location 832b, the arrival of the contrast agent in the window is detected by the motion detection means 806, 896 as a change in the brightness of the image within the window (see FIGS. 7–9). When the motion detection means 806, 896 indicates that motion or change has been observed, the imaging system performs the user-programmed radiographic exposure; the imaging system then advances to the location associated with the next programmed step and again awaits the detection of the contrast medium.

When operating in the two-window mode, the imaging system 100 uses motion detected in the first defined window 820 at location 832b as a trigger to initiate operation using the motion-specific fluoroscopic parameters (i.e., higher pulse rate, lower frame integration, higher edge enhancement). As the contrast medium progresses to location 832c, the imaging system waits. When the contrast medium progresses to location 832d, motion or change is detected in the second defined window 830, and the imaging system performs the programmed radiographic exposure step. As the contrast medium progresses to location 832e, the imaging system moves to the location of the next user-programmed examination step. When the operator elects to use more than two windows, a similar method is used.

In step 860, the user employs the motion detection user interface 458 (FIGS. 2, 8) to select an image variation threshold for use by the motion detection means 806, 896. The motion detection means 806, 896 monitors the changes in brightness (or another parameter) of an input image signal within the user selected windows. If the changes exceed the image variation threshold selected by the user, the motion detection means 806, 896 interpret such changes as motion and provide an indication that motion is detected to the control system 510.

In step 862, the user may select whether the imaging system operates in "Stepping" or "Follow" mode. The "Stepping" mode employs discrete positioning of the imaging system. For each predefined step (described above in connection with step 856), fluoroscopy is used to observe the progress of the contrast medium to the end of the viewing area, and a radiographic exposure is made. The system then moves to the next step position. The "Follow" mode employs continuous positioning of the imaging system. Fluoroscopy is used to observe the progress of the contrast medium, and the imaging system is continuously positioned to maintain the contrast medium within the viewing area. When the imaging system reaches certain user-programmed locations, radiographic exposures are made.

In step 864, the control system 510 determines whether the operator has requested the fluoroscopic examination to begin. If not, the method loops back to step 846 and repeats. If the operator has requested fluoroscopic examination to begin, the method continues in step 866, in which the control system commences the fluoroscopic exposure. In step 868, the control system waits until the ABS 204 reaches a stable operating condition. At step 872 the control system records and maintains the x-ray tube voltage level, effectively disabling the ABS 204. This step is required because otherwise the ABS 204 would seek to maintain a consistent image brightness as the contrast medium arrives, thereby defeating the motion detection means 806, 896. See result block 870.

In step 874, the motion detection means 806, 896 determines whether any variation in the image which have occurred in window 1 820 exceeds the threshold selected by the user in step 860. The system waits until the image variation exceeds the threshold, and then progress to step 876, in which the motion detection means 806, 896 provides an indication that motion has been detected in window 1 820. See result block 878.

In step 880, the system determines whether the operator has selected the one-window mode or the two-window mode. If the operator has selected the one-window mode, the motion detection signal means that the contrast medium has appeared in the area of interest. Therefore, the method continues at step 884, which is the beginning of a sequence of steps in which the system performs the operator-programmed radiographic exposure and moves to a next desired examination location.

If the operator has selected the two-window mode, the motion detection signal means that the contrast medium is present in the image, but the imaging system must wait until the contrast medium has reached the area of interest (i.e., the end of the viewing area) before performing the radiographic exposure. The method continues at step 902. In steps 902, 904, and 906, the control system 510 changes the fluoroscopic examination parameters to those suited for observing motion (see steps 730–736, FIG. 4*b*). In step 902, the control system increases the fluoroscopic pulse rate. In step 904, the control system reduces or the frame integration rate (or eliminates frame integration altogether). In step 906, the control system enables or increases the edge enhancement level. As shown by result block 898 and 908, steps 902, 904, and 906 improve the quality of the diagnostic image, and eliminate motion artifacts.

In step 910, the motion detection means 806, 896 determines whether any variation in the image which have occurred in window 2 830 exceeds the threshold selected by the user in step 860. The system waits until the image variation exceeds the threshold, at which time the motion detection means 806, 896 provides an indication that motion has been detected in window 2 830. As shown in result block 912, the motion detection signal means that the contrast medium has now progressed to the end of the viewing area. Therefore, the method continues at step 884, which is the beginning of a sequence of steps in which the system performs the operator-programmed radiographic exposure and moves to a subsequent desired examination location.

In step 884, the radiographic exposure is performed. In step 886, the control system 501 determines whether the "stepping" mode has been selected. If the stepping mode has been selected, the method continues at step 888. The control system 501 determines whether the current stepping program has completed. If the stepping program has been completed, the method jumps back to step 864 to wait for the operator to initiate another fluoroscopic examination. If the stepping program has not been completed, the method continues in step 890. The imaging system advances to the user-selected location associated with next programmed examination step. This location may be explicitly programmed by the user, or it may be calculated by the imaging system according to user-selected parameters. The method then jumps back to step 864 to wait for the operator to initiate the fluoroscopic examination portion of the next programmed examination step.

If, in step 886, the control system 510 determines that the "stepping" mode was not selected, the method continues at step 892. The control system determines whether the "follow" mode was selected. If the "follow" mode was not selected, then the method jumps back to step 864 to wait for the operator to initiate another fluoroscopic examination. However, if the "follow" mode was selected, then step 894 is performed. The control system 510 uses information from the video signal produced by the fluoroscopy system and the motion detection means to continuously reposition the digital imaging platform 114 to follow the progression of the contrast medium through the patient's body. The control system 510 uses servo control techniques to automatically move the digital imaging platform to maintain the video image variation at the threshold level, thereby maintaining the contrast medium in the center of the fluoroscopic image. As the digital imaging platform 114 follows the contrast medium, the control system 510 periodically initiates radiographic exposures. The "Follow" mode terminates upon operator request or when the contrast medium and digital imaging platform have reached the programmed examination zone. When the "Follow" mode is terminated, the method jumps back to step 864 to wait for the operator to initiate another fluoroscopic examination.

According to an aspect of the present invention, the imaging system 100 may analyze a video signal representing an acquired x-ray or optical image to detect motion or another significant change in the image. The resulting motion detection signal may be used to control the operation of the imaging system, providing certain automatic features which provide high image quality while advantageously reducing the x-ray dose delivered to the patient and the operator.

FIG. 7 is a flow chart illustrating a first exemplary method for use with the inventive imaging system 100 for detecting motion or other changes in a stream of video image information, in which the method may be performed in conjunction with programmable processor components of a general-purpose commercially-available image processor. Thus, a suitable general-purpose commercially-available image processor, and the method of FIG. 7, may be used to implement to motion detection means 496 of FIG. 2. The result from the motion detection method of FIG. 7 may be used with the methods of FIGS. 4 and 6 to enable the imaging system to provide certain automatic operations in coordination with the detected movement. The image processor may provide a variety of functions in addition to motion detection.

For simplicity, the following discussion of FIG. 7 assumes that an entire image processor, including any required input or output signal conversion equipment, is dedicated to the motion detection method 920 shown therein, for a single video signal. However, one of skill in the art will recognize how an image processor might handle motion detection (or other functions) for multiple signals using well-known multi-tasking techniques, and how multiple image processors could also be used to service additional channels.

Although the internal organization of commercially available image processors may vary, the image processing functions are generally performed using digital processing techniques. In the discussion below, it is assumed that the image processor has at least the following facilities, which are believed to be commonly provided in commercial image processors: (a) suitable means for converting an input video signal into digital data representing the amplitude of the signal or the luminance of the image at an array of image locations; (b) means for storing at least two successive frames of the video signal; (c) processing means, related memory, and input/output having at least the capabilities of a basic microprocessor-based computer; and (d) the ability to generate an output video signal as modified by processing.

The method 920 start in step 922. In step 924, the processor determines whether the user has selected a "test" mode for setting-up and adjusting windows of interest in motion detection (see windows 820, 830 of FIG. 5), or an operational mode. If the user has selected the test mode, the method continues with step 926. A first video frame is captured from the input video signal and digitized. In step 928, the digitized image is stored in a video memory. In step 930, a subset of the memory representing a portion of the image is defined as a window. In its simplest form, as shown by window 820 (FIG. 5), the window may be rectangular, having left-hand, right-hand, top, and bottom edges 812, 814, 816, and 818 respectively. However, other shapes could also be used. In addition, more than one window may be generated (see FIG. 5).

In step 932, the shape of the window is displayed to the user over the digitized image. Several methods are known in the art for displaying the window shape to the user. For example, all of the pixels forming the window may be illuminated, the pixels at the window borders may be illuminated, or the window may be highlighted by increasing the luminance of each pixel in the window by a predefined amount.

In step 934, the processor determines whether a window adjustment request, such as a change in the controls of the motion detection user interface 458, is pending. If a request is pending, then in step 936, the window size, shape, or position is changed accordingly, and in step 938, the motion detect threshold level is defined. The method then continues in step 940. If, in step 934, no window adjustment request was pending, the method jumps directly to step 940.

In step 940, the processor determines whether the user has requested to exit the set-up mode. If the user has not made such a request, then the method returns to step 934 to await another window adjustment request. Otherwise, the method continues at step 942.

If, in step 924, the processor determines that the user did not select the test or set-up mode, then the method jumps directly to step 942. Step 942 is the first in a sequence of steps in which the actual motion detection function is performed. In step 942, a first frame of image information is captured and digitized. In step 944, the digitized image is stored in a first video memory location "A". In step 946, the processor establishes a selected characteristic of the image in video memory location "A" as reference or baseline level for the image in the window, against which subsequent frames of video information will be compared in order to detect change. The selected image characteristic may be, for example, the integrated brightness of that portion of the image which is within the user-defined window. In step 948, the next frame of image information is captured and digitized. In step 950, the digitized image is stored in second video memory location "B".

In step 952, the processor compares the selected charateristics of the two images in memory locations "A" and "B," considering only those portions of the images within the defined window. The result of the comparison is a value representing the difference between the two images. In step 954, the processor determines whether the image difference value produced in the comparison exceed the user-selected image variation threshold level. If the image difference value exceeds the threshold, then step 956 is performed, and the image processor produces the "motion detected" signal. If the image difference value does not exceed the threshold, then the method jumps to 948 to repeat the process. A new image is acquired and saved; the comparison with the reference value is performed; and this process is repeated until motion is detected.

FIG. 8 is a block diagram showing the organization of a motion detection circuit or module 410 for use in detecting motion or change in a stream of video image information. FIG. 9 is a flow chart illustrating a second exemplary method 958 for use with the inventive imaging system 100 for detecting motion or other changes in a stream of video image information, in which the method may be performed in conjunction with the motion detection system of FIG. 8. The result from either of the motion detection methods of FIG. 7 or 9 may be used with the methods of FIGS. 4 and 6 to enable the imaging system to provide certain automatic operations in coordination with the detected movement.

As best seen in FIG. 8, the motion detection module 410 receives one or more video signals, such as 412, 414, from optical camera 408 and image intensifier 166, respectively, by means of an input amplifier 416. The input amplifier selects one of the input signals for use, amplifies it, and supplies the selected, amplified output on lead 418 to a black-level restoration means 424, a synchronization impulse separator means 420, and an output video amplifier/mixer means 440. The black-level restoration means 424 clamps the black level (i.e., the minimum-luminance or baseline level) of the input video signal to a standard reference level. This provides a stable reference for future signal processing. The output of the black-level restoration means 424 is a restored video signal provided on lead 426 to the window generator 428 and to a window integrator 444.

A motion detection user interface 458 allows the user to control the location and size of each window of interest (820, 830; FIG. 5) in motion detection. The motion detection module 410 is shown with capabilities to process a single video signal at one time, and to consider motion in a single window. However, the motion detection module 410 may be expanded to process multiple video signals simultaneously by duplicating all of the circuitry for each required video signal. Each motion detection module may be expanded to consider motion in multiple windows by duplicating the window generator 428, window integrator 444, sample and hold 450, and window comparator 456 for each required window. The motion detection user interface 458 provides the location and size of the window, as specified by the user, to the window adjustments control 476, over lead 474. For example, the user may use the controls to specify the vertical and horizontal locations of each of two opposing corners of the window. Alternatively, the controls 464, 466, 468, and 470 may specify the vertical and horizontal position of corner of the window, along with the width and height of the window.

The synchronization impulse separator means 420 extracts vertical and horizontal synchronization pulse information from the amplified video signal 418. The extracted synchronization information is supplied to control logic 420, sample and hold circuit 450, and window generator means 428, via leads 422, 454. The synchronization information allows components of the motion detection module 410 to correlate a position in the video image with a time offset from the beginning of each frame of the video signal. The control logic 430 produces control signals 432 which are supplied to a window brightness control means 434.

The window adjustments control provides the location and size of the window to the window generator 428 via lead 478. The window generator uses this information, in conjunction with the synchronization signals to produce a window borders output signal 442 which indicates when the restored video signal 426 contains image information which is within the window. The window generator 428 contains programmable counters. By counting the number of horizontal synchronization impulses (or horizontal lines) from the vertical synchronization impulse (which represents the start of the frame), particular horizontal lines are selected as upper and lower borders of the window. Horizontal synchronization counters #1 and #2 perform this function. By counting time from the beginning of the horizontal synchronization impulse, particular positions on the horizontal line are selected as the left and right borders of the window. Time counters #1 and #2 perform this function.

The window integrator 444 receives the restored video signal 426 and the window borders signal 442 and performs an integration of the brightness of the image represented by the video signal, but only when the video signal contains information which is within the window, as enabled by the window borders signal 442. Thus, the output signals 446, 448 of the window integrator 444 describe the integrated brightness of just that portion of the video image which is within the window.

The window brightness control means 434 receives a signal 436 from the window generator 428 indicating when the video signal represents image information corresponding to locations within the window. The window brightness control 434 operates in the set-up mode produces an "additional brightness" signal 438 to the output video amplifier/mixer means 440, indicating when the video signal corresponds to a location inside the window. The output video amplifier/mixer means 440 uses the amplified composite video signal 418 and the "additional brightness" signal 438 to produce an output video signal 488 which is supplied to the video monitor 486. The output video signal 488 is similar to the input signal, but its brightness is enhanced whenever the "additional brightness" signal 438 is enabled. Thus, the portion of the image within the window appears brighter than the remainder of the window. When the set-up mode is enabled, this feature allows the user to observe where the borders of the window are located, permitting convenient adjustment thereof.

The sample and hold circuit 450 is responsive to a signal 454 from the synchronization pulse separator 420. A sample-and-hold circuit 450 samples the output signal 446 from the window integrator 444 at the beginning of each new video frame. Thus, at the end of each video frame, the window integrator output signal 448 presents the window-limited integrated brightness of the current video frame, and the sample and hold circuit output signal 452 presents the window-limited integrated brightness of the previous video frame. Signals 448 and 452 are provided to the window comparator 456. The motion detection user interface 458 provides motion detect threshold level, as specified by the operator, to the window comparator 456. If the difference between signals 448 (current frame brightness) and 452 (previous frame brightness) exceeds the motion detect threshold level selected by the operator, then the window comparator asserts the motion detect signal 482.

FIG. 9 is a flow chart illustrating a second exemplary method 958 for use with the inventive imaging system 100 for detecting motion or other changes in a stream of video image information. The method 958 of FIG. 9 may be performed in conjunction with the motion detection system 410 of FIG. 8, or with any other suitable video signal processing means.

The method 958 starts at step 960. In step 962, the input image signal is buffered and amplified. In step 964, the black level of the amplified video signal is restored to a standard baseline level. In step 966, the vertical and horizontal synchronization pulses are extracted from the video signal.

In step 968, a test is made to determine whether the motion detection module 410 is in a test or "set-up" mode, or in the operating mode. If the motion detection module is in the set-up mode, the method continues in step 970.

In step 970, horizontal line counter #1 is programmed for the line number corresponding to the upper border of the window. In step 972, horizontal line counter #2 is programmed for the line number corresponding to the lower border of the window. In step 974, time counter #1 is programmed for the pixel clock value corresponding to the left border of the window. In step 976, time counter #2 is programmed for the pixel clock value corresponding to the left border of the window. In step 978, the window is displayed or highlighted on the image. For example, the brightness of the video signal may be increased whenever the signal corresponds to image locations within the window.

In step 980, a test is made to determine whether a window adjustment request, such as a change in the controls of the motion detection user interface 458, is pending. If a request is pending, then in step 982, the window size, shape, or position is changed accordingly, and in step 984, the motion detect threshold level is defined. The method then continues in step 980. If, in step 980, no window adjustment request was pending, the method jumps directly to step 986.

In step 986, a test is made to determine whether the user has requested to exit the set-up mode. If the user has not made such a request, then the method returns to step 980 to await another window adjustment request. Otherwise, the method continues at step 988.

If, in step 968, it is determined that the motion detection module is not in the test or set-up mode, then the method jumps directly to step 988. In step 988, that portion of the first frame of the video signal which is located within the user-selected window is integrated to determine an integrated window brightness. In step 990, the integrated window brightness of the first frame of the video signal is established as a reference or baseline level for the image in the window. In step 992, that portion of the "next" frame of the video signal which is located within the user-selected window is integrated to determine an integrated window brightness.

In step 994, the reference integrated window brightness value determined from the first frame of the video signal is subtracted from the integrated window brightness value determined from the "next" frame. The result represents the difference in window brightness between the reference frame and the next frame. In step 996, the brightness difference value is compared with the motion detect threshold level defined in step 984. If the difference value exceeds the threshold, then step 998 is performed and the motion detection module asserts the "motion detected" signal. However, if the difference value does not exceed the threshold, then the method jumps to 988 to repeat the process. Steps 988–996 are repeated on successive frames of the video signal until motion is detected.

The above-described embodiments of the invention are merely examples of ways in which the invention may be carried out. Other ways may also be possible, and are within the scope of the following claims defining the invention.

What is claimed is:

1. A diagnostic medical imaging system adapted for radiographic and fluoroscopic examinations, said system being capable of operating in a fluoroscopic examination mode and in a radiographic examination mode, comprising:

X-ray tube means;

means for receiving x-rays;

said X-ray tube means delivering an x-ray output which is responsive at least in part to filament current provided to said X-ray tube and high-voltage power supply provided to said x-ray tube;

said output of said X-ray tube being responsive to a change in said filament current by gradually approaching an output level corresponding to said change over a time interval;

said output of said X-ray tube being essentially immediately responsive to a change in said high-voltage power supply;

fluoroscopic examination mode x-ray output set point means;

means, operable during a fluoroscopic examination and including automatic brightness control means, for establishing fluoroscopic-mode preferred values for said filament current and said high-voltage power supply;

means operable during a radiographic examination for operating said x-ray tube means at predetermined values of said filament current and said high-voltage power supply;

means responsive to said predetermined value of said filament current and said fluoroscopic examination mode x-ray output set point means for determining a fluoroscopic mode initial value for said high-voltage power supply which is required to cause said x-ray tube to produce an x-ray output approximating said set point during an initial period after a change occurs in said filament current from said radiographic mode predetermined value to said fluoroscopic-mode preferred value;

means responsive to an instruction to transition from said radiographic examination mode to said fluoroscopic examination mode for rapidly causing said x-ray tube means to operate according to said fluoroscopic mode initial value of said high-voltage power supply and said fluoroscopic-mode preferred value for said filament current;

means responsive to the output of said x-ray tube means for adjusting the high-voltage power supply as needed to maintain said x-ray output at said desired fluoroscopic mode x-ray output.

2. A diagnostic medical imaging system adapted for radiographic and fluoroscopic examinations, said system being capable of operating in a fluoroscopic examination mode and in a radiographic examination mode, comprising:

means for producing x-rays directed toward an examination region of interest;

means for receiving x-rays;

said means for producing x-rays delivering an x-ray output which is responsive at least in part to first and second controllable electrical parameters;

said output of said means for producing x-rays being responsive to a change in said first controllable electrical parameter by approaching an output level corresponding to said change over a time interval;

said output of said means for producing x-rays being essentially immediately responsive to a change in said second electrical parameter;

means for establishing a desired fluoroscopic mode x-ray output to be delivered while in said fluoroscopic examination mode;

means operable during a fluoroscopic examination for establishing a fluoroscopic-mode preferred value for said first electrical parameter;

means operable during a radiographic examination for operating said means for producing x-rays at a predetermined value of said first parameter;

means responsive to said predetermined value of said first electrical parameter and said desired fluoroscopic mode x-ray output for determining a fluoroscopic mode initial value for said second electrical parameter which is required to cause said means for producing x-rays to produce an x-ray output approximating said desired fluoroscopic mode x-ray output during an initial period after a change occurs in said first electrical parameter from said radiographic mode predetermined value;

means responsive to an instruction to transition from said radiographic examination mode to said fluoroscopic examination mode for rapidly causing said means for producing x-rays to operate according to said fluoroscopic mode initial value of said second electrical parameter and said fluoroscopic-mode preferred value for said first electrical parameter.

3. A diagnostic medical imaging system adapted for radiographic and fluoroscopic examinations, said system being capable of operating in a fluoroscopic examination mode and in a radiographic examination mode, comprising:

means for producing x-rays directed toward an examination region of interest;

means for receiving x-rays;

said means for producing x-rays delivering an x-ray output which is responsive at least in part to first and second controllable electrical parameters;

said output of said means for producing x-rays being responsive to a change in said first controllable electrical parameter by approaching an output level corresponding to said change over a time interval;

said output of said means for producing x-rays being essentially immediately responsive to a change in said second electrical parameter;

means for establishing a desired fluoroscopic mode x-ray output to be delivered while in said fluoroscopic examination mode;

means operable during a fluoroscopic examination for establishing a fluoroscopic-mode preferred value for said first electrical parameter;

means operable during a radiographic examination for operating said means for producing x-rays at a predetermined value of said first parameter;

means responsive to an instruction to transition from said radiographic examination mode to said fluoroscopic examination mode for rapidly causing said means for producing x-rays to operate according to said fluoroscopic-mode preferred value for said first electrical parameter;

means responsive to the output of said means for producing x-rays for adjusting said second electrical parameter as needed to maintain said x-ray output at said desired fluoroscopic mode x-ray output.

4. For use with a radiographic/fluoroscopic diagnostic imaging system having a radiographic exposure mode, a fluoroscopic exposure mode, x-ray emitting means, said x-ray emitting means having an x-ray output level responsive substantially instantaneously to a first electrical power supply parameter; said x-ray emitting means having an x-ray output level responsive to a second electrical power supply parameter; the method of rapidly transitioning from said radiographic to fluoroscopic imaging mode comprising the steps of:

(a) establishing a desired value of said x-ray output level during said fluoroscopic exposure mode;

(b) determining a value of said second parameter which was used during said radiographic exposure mode;

(c) determining an initial value for said first parameter which will result in said x-ray emitting means producing said desired value of said x-ray output level when said x-ray emitting means operates at said determined value of said second parameter;

(d) initiating a change in said second parameter to a value appropriate for said fluoroscopic imaging mode;

(e) changing said first parameter to said determined initial value for said first parameter; and (f) measuring said x-ray output level and responsively adjusting said first parameter to cause said x-ray output level to approximate said desired value thereof.

5. For use with a radiographic/fluoroscopic diagnostic imaging system having a radiographic exposure mode, a fluoroscopic exposure mode, and x-ray emitting means, said x-ray emitting means having an x-ray output level responsive substantially instantaneously to a first electrical power supply parameter; said x-ray emitting means having an x-ray output level substantially non-instantaneously responsive to a second electrical power supply parameter; a method of rapidly transitioning from said fluoroscopic to radiographic imaging mode of the type including the steps of:

(a) establishing a desired x-ray dose;

(b) maintaining said first parameter at a level used during said fluoroscopic exposure mode;

(c) changing said second parameter to a value appropriate for said radiographic exposure mode;

(d) measuring an accumulated x-ray dose delivered by said x-ray emitting means;

(e) and terminating said radiographic exposure mode when said measured accumulated x-ray dose equals or exceeds said desired x-ray dose;

wherein the improvement comprises measuring said accumulated x-ray dose as an integrated measurement of an electrical parameter of the energy supplied to said x-ray emitting means.

6. A diagnostic medical imaging system adapted for radiographic and fluoroscopic examinations, said system being capable of operating in a fluoroscopic examination mode and in a radiographic examination mode, comprising:

means for producing x-rays directed toward an examination region of interest;

means for receiving x-rays;

said means for producing x-rays delivering an x-ray output which is responsive at least in part to first and second controllable electrical parameters;

said output of said means for producing x-rays being responsive to a change in said first controllable electrical parameter by gradually approaching an output level corresponding to said change over a time interval;

said output of said means for producing x-rays being essentially immediately responsive to a change in said second electrical parameter;

means operable during a fluoroscopic examination for establishing fluoroscopic-mode preferred values for said first and second electrical parameters;

means for establishing a desired radiographic mode x-ray output and a desired radiographic mode x-ray dose to be delivered while in said radiographic examination mode;

means responsive to said fluoroscopic-mode preferred values and said desired radiographic mode x-ray output for determining radiographic mode preferred values for said first and second electrical parameters;

means responsive to an instruction to transition from said fluoroscopic examination mode to a radiographic examination mode for rapidly causing said means for producing x-rays to operate according to said radiographic mode preferred values for said first and second electrical parameters; and radiographic exposure termination means responsive to the output of said means for producing x-rays for restoring operation thereof according to previous values of said first and second electrical parameters when said desired radiographic mode x-ray dose has been delivered.

7. The imaging system of claim 6 wherein said means for producing X-rays is an X-ray tube.

8. The imaging system of claim 7 wherein said first controllable electrical parameter is filament current provided to said X-ray tube.

9. The imaging system of claim 7 wherein said second controllable electrical parameter is the high-voltage power supply provided to said X-ray tube.

10. The imaging system of claim 6 wherein said means operable during a fluoroscopic examination for establishing fluoroscopic-mode preferred values for said first and second electrical parameters includes an automatic brightness system.

11. The system of claim 6 wherein said radiographic exposure termination means comprises an automatic exposure control system.

12. A diagnostic medical imaging system adapted for radiographic and fluoroscopic examinations of a patient, said system being capable of operating in a fluoroscopic examination mode and in a radiographic examination mode, said system being of the type including:

means for producing x-rays directed toward an examination region of interest;

means for receiving x-rays and producing therefrom image information relating to said examination region of interest;

means for deriving movement related information producing an indication when movement of said patient with respect to said imaging system, requests for movement of said patient with respect to said imaging system, or change in a visible feature of said image information occur;

means responsive to said means for deriving movement related information for operating said imaging system in said fluoroscopic examination mode while said indication is absent; and means responsive to said means for deriving movement related information for performing a radiographic exposure when said indication is received;

wherein the improvement comprises:

first image change detection means responsive to image change in a first selected image region for producing a first signal indicating said change;

second image change detection means responsive to image change in a second selected image region for producing a second signal indicating said change;

means for initially causing said imaging system to operate according to a first set of fluoroscopic and imaging operating parameters;

means responsive to said first signal for causing said imaging system to operate according to a second set of fluoroscopic and imaging operating parameters non-identical with said first set; and means responsive to said second signal for initiating a radiographic exposure.

13. A method for use with a diagnostic medical imaging system adapted for radiographic and fluoroscopic examinations of a patient, said system being capable of operating in a fluoroscopic examination mode and in a radiographic examination mode, said system having means for collecting image information from said patient to form a representation of an image; the method including the steps of:

a) establishing fluoroscopic and imaging operating parameters;

(b) defining at least one region of said representation of an image;

(c) performing the fluoroscopic examination;

(d) detecting image change in at least one of said defined regions of said representation of an image; and (e) causing said imaging system to initiate a radiographic exposure;

wherein the improvement comprises:

step (a) further comprising the step of (a1) defining initial fluoroscopic and imaging examination parameters;

step (b) further comprising the step of (b1) defining at least first and second regions of said representation of an image;

step (c) further comprising the steps of:

(c1) initiating the fluoroscopic examination according to the initial fluoroscopic and imaging examination parameters; and (c2) detecting image change in said first defined region of said representation of an image, and responsive thereto, causing said imaging system to operate according to adjusted fluoroscopic and imaging examination parameters;

step (d) further comprising in the step of (d1) detecting image change in said second defined region of said representation of an image; and step (e) further comprising in the step of (e1) responsive thereto, causing said imaging system to initiate said radiographic exposure.

14. A diagnostic medical imaging system adapted for radiographic and fluoroscopic examinations, said system being capable of operating in a fluoroscopic examination mode and in a radiographic examination mode, comprising:

means for producing x-rays directed toward an examination region of interest;

means for receiving x-rays;

said means for producing x-rays delivering an x-ray output which is responsive at least in part to first and second controllable electrical parameters;

said output of said means for producing x-rays being responsive to a change in said first controllable electrical parameter by gradually approaching an output level corresponding to said change over a time interval;

said output of said means for producing x-rays being essentially immediately responsive to a change in said second electrical parameter;

means for establishing a desired fluoroscopic mode x-ray output to be delivered while in said fluoroscopic examination mode;

means operable during a fluoroscopic examination for establishing fluoroscopic-mode preferred values for said first and second electrical parameters;

means operable during a radiographic examination for operating said means for producing x-rays at predetermined values of said first and second electrical parameters;

means responsive to said predetermined value of said first electrical parameter and said desired fluoroscopic mode x-ray output for determining a fluoroscopic mode initial value for said second electrical parameter which is required to cause said means for producing x-rays to produce an x-ray output approximating said desired fluoroscopic mode x-ray output during an initial period after a change occurs in said first electrical parameter from said radiographic mode predetermined value to said fluoroscopic-mode preferred value;

means responsive to an instruction to transition from said radiographic examination mode to said fluoroscopic examination mode for rapidly causing said means for producing x-rays to operate according to said fluoroscopic mode initial value of said second electrical parameter and said fluoroscopic-mode preferred value for said first electrical parameter;

means responsive to the output of said means for producing x-rays for adjusting said second electrical parameter as needed to maintain said x-ray output at said desired fluoroscopic mode x-ray output.

15. The imaging system of claim 14 wherein said means operable during a fluoroscopic examination for establishing fluoroscopic-mode preferred values for said first and second electrical parameters comprises an automatic brightness system.

16. The imaging system of claim 14 wherein said means responsive to the output of said means for producing x-rays for adjusting said second electrical parameter to cause said x-ray output as needed to maintain said desired fluoroscopic mode x-ray output comprises an automatic brightness system.

17. The imaging system of claim 14 wherein said means for producing X-rays is an X-ray tube.

18. The imaging system of claim 17 wherein said first controllable electrical parameter is filament current provided to said X-ray tube.

19. The imaging system of claim 17 wherein said second controllable electrical parameter is the high-voltage power supply provided to said X-ray tube.

* * * * *

UNITED STATES PATENT AND TRADEMARK OFFICE
CERTIFICATE OF CORRECTION

PATENT NO. : 5,917,882
DATED      : June 29, 1999
INVENTOR(S): Khutoryansky et al.

Page 1 of 14

It is certified that error appears in the above-identified patent and that said Letters Patent is hereby corrected as shown below:

IN THE DRAWINGS

Delete Drawing Sheets 2-7, and 9-14, and substitute therefor the Drawing Sheets, consisting of FIGS. 2, 3A, 3B, 3C, 4A, 4B, 6A, 6B, 6C, 7, 8, and 9, as shown on the attached pages.

Column 2, line 30, insert --to-- between "need" and "move";

Column 5, line 18, insert --)-- after the first "mA*S";

Column 19, line 23, change "N.Y." to --NY--;

Column 19, line 25, change "Wis." to --WI--;

Column 21, line 34, insert --mA*S-- after "desired" and insert --x-ray-- before "dose";

Column 21, lines 46-47, delete "Thus, the requirements ... transition.";

Column 30, line 62, change "progress" to --progresses--;

Column 32, line 28, change "to" to --the--;

Column 32, line 58, change "start" to --starts--;

Column 35, line 17, insert --and-- between "mode" and "produces"; and

UNITED STATES PATENT AND TRADEMARK OFFICE
CERTIFICATE OF CORRECTION

PATENT NO. : 5,917,882
DATED : June 29, 1999
INVENTOR : Khutoryansky et al.

Page 2 of 14

It is certified that error appears in the above-identified patent and that said Letters Patent is hereby corrected as shown below:

Column 36, line 7, change "left" to --right--.

Signed and Sealed this

First Day of February, 2000

Q. TODD DICKINSON

*Attest:*

*Attesting Officer*   Acting Commissioner of Patents and Trademarks

SYSTEM CONTROL BLOCK DIAGRAM